(12) United States Patent
Mukumoto

(10) Patent No.: US 9,865,060 B2
(45) Date of Patent: Jan. 9, 2018

(54) X-RAY COMPUTED-TOMOGRAPHY APPARATUS AND IMAGING-CONDITION-SETTING SUPPORT APPARATUS

(71) Applicant: Toshiba Medical Systems Corporation, Otawara-shi (JP)

(72) Inventor: Go Mukumoto, Iwata (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 184 days.

(21) Appl. No.: 14/692,135

(22) Filed: Apr. 21, 2015

(65) Prior Publication Data

US 2015/0297157 A1 Oct. 22, 2015

(30) Foreign Application Priority Data

Apr. 21, 2014 (JP) ................. 2014-087764

(51) Int. Cl.
G06T 7/00 (2017.01)
A61B 6/00 (2006.01)
G06T 11/00 (2006.01)
A61B 6/03 (2006.01)

(52) U.S. Cl.
CPC ............ *G06T 7/0048* (2013.01); *A61B 6/032* (2013.01); *A61B 6/4035* (2013.01); *A61B 6/465* (2013.01); *A61B 6/481* (2013.01); *A61B 6/5205* (2013.01); *A61B 6/545* (2013.01); *G06T 11/003* (2013.01); *A61B 6/469* (2013.01); *A61B 6/5217* (2013.01)

(58) Field of Classification Search
CPC ....... A61B 6/032; A61B 6/4035; A61B 6/465; A61B 6/481; A61B 6/5205; A61B 6/469; A61B 6/5217; G06T 7/0048; G06T 11/003
See application file for complete search history.

(56) References Cited

U.S. PATENT DOCUMENTS

| | | | |
|---|---|---|---|
| 7,657,074 B2 | 2/2010 | Haras | |
| 7,995,819 B2* | 8/2011 | Vaillant | A61B 6/032 128/922 |
| 8,953,856 B2* | 2/2015 | Ostrovsky-Berman | G06T 7/0032 382/128 |
| 2003/0108149 A1* | 6/2003 | Tsuyuki | A61B 6/032 378/54 |

(Continued)

FOREIGN PATENT DOCUMENTS

| JP | 07-023946 | 1/1995 |
|---|---|---|
| JP | 2006-192270 | 7/2006 |

(Continued)

*Primary Examiner* — David E Smith
(74) *Attorney, Agent, or Firm* — Oblon, McClelland, Maier & Neustadt, L.L.P.

(57) ABSTRACT

In an X-ray computed-tomography apparatus of an embodiment, a reconstruction processing unit reconstructs image data based on projection data that is generated from output of an X-ray detector. A specifying unit specifies a scan position or a scan range for main scanning. A changing unit identifies characteristic points based on a structure inside the subject from image data, and changes the scan position or the scan range specified by the specifying unit based on a result of checking data relating to the characteristic points and data relating to corresponding anatomical characteristic points in a virtual subject against each other.

18 Claims, 16 Drawing Sheets

(56) References Cited

U.S. PATENT DOCUMENTS

| | | | | |
|---|---|---|---|---|
| 2009/0141854 A1* | 6/2009 | Hirokawa | ............... | A61B 6/032 378/4 |
| 2011/0091008 A1* | 4/2011 | Hirokawa | ............... | A61B 6/032 378/4 |
| 2013/0216019 A1* | 8/2013 | Maeda | .................... | A61B 6/484 378/19 |
| 2014/0133622 A1* | 5/2014 | Yin | ........................ | A61B 6/032 378/8 |
| 2015/0139520 A1* | 5/2015 | Senegas | ................ | G06T 7/0014 382/131 |
| 2015/0157207 A1* | 6/2015 | Ikeda | ..................... | A61B 6/545 600/410 |

FOREIGN PATENT DOCUMENTS

| | | |
|---|---|---|
| JP | 2007-275216 | 10/2007 |
| JP | 2008-012171 | 1/2008 |

\* cited by examiner

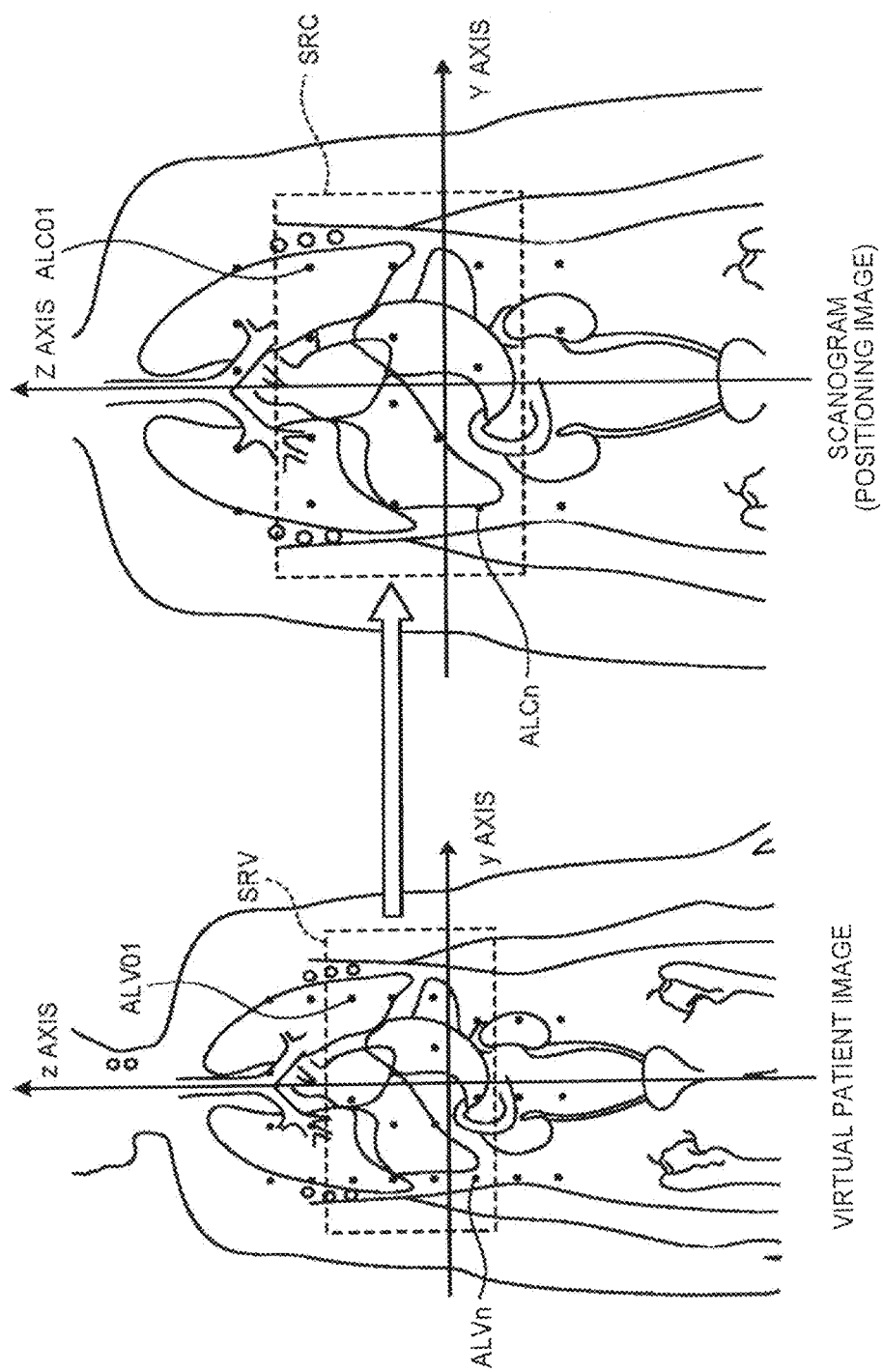

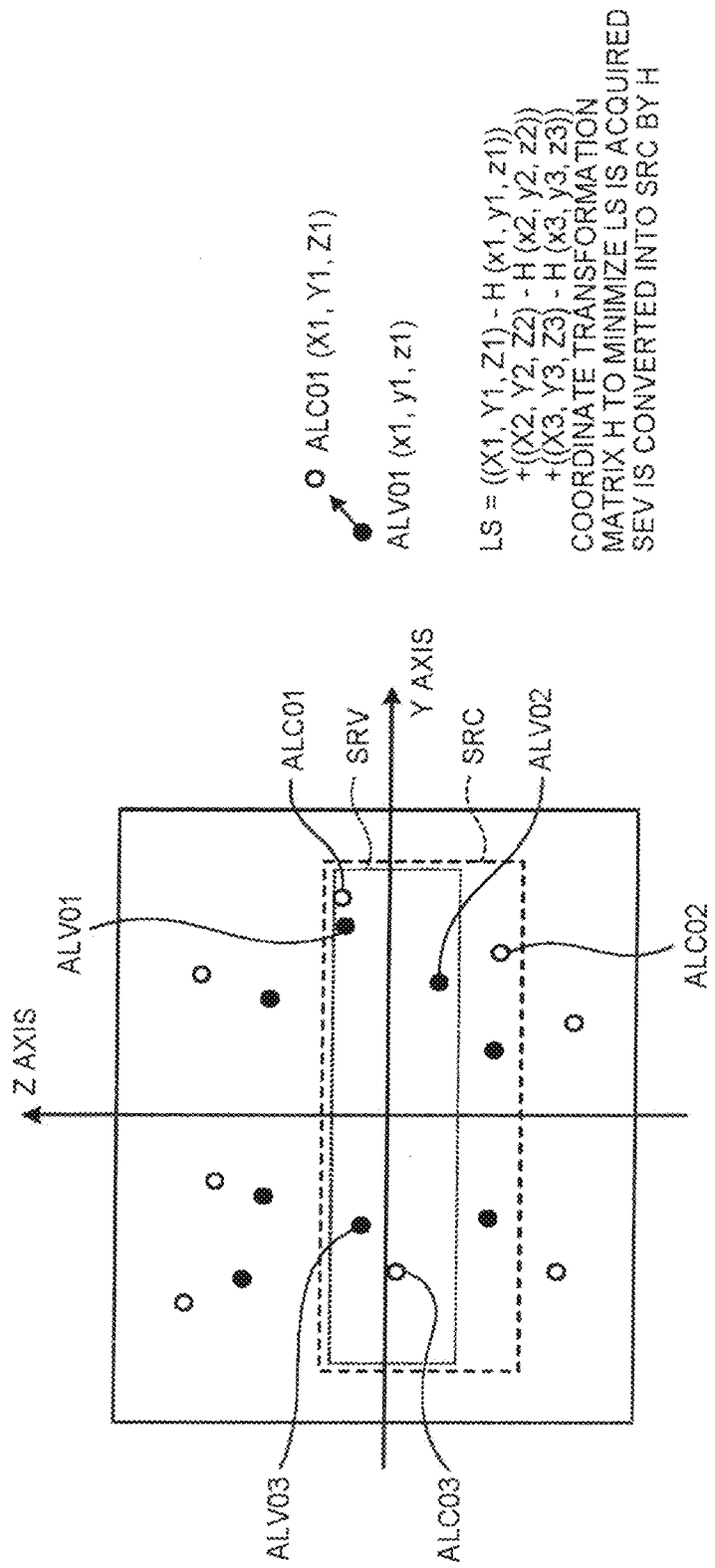

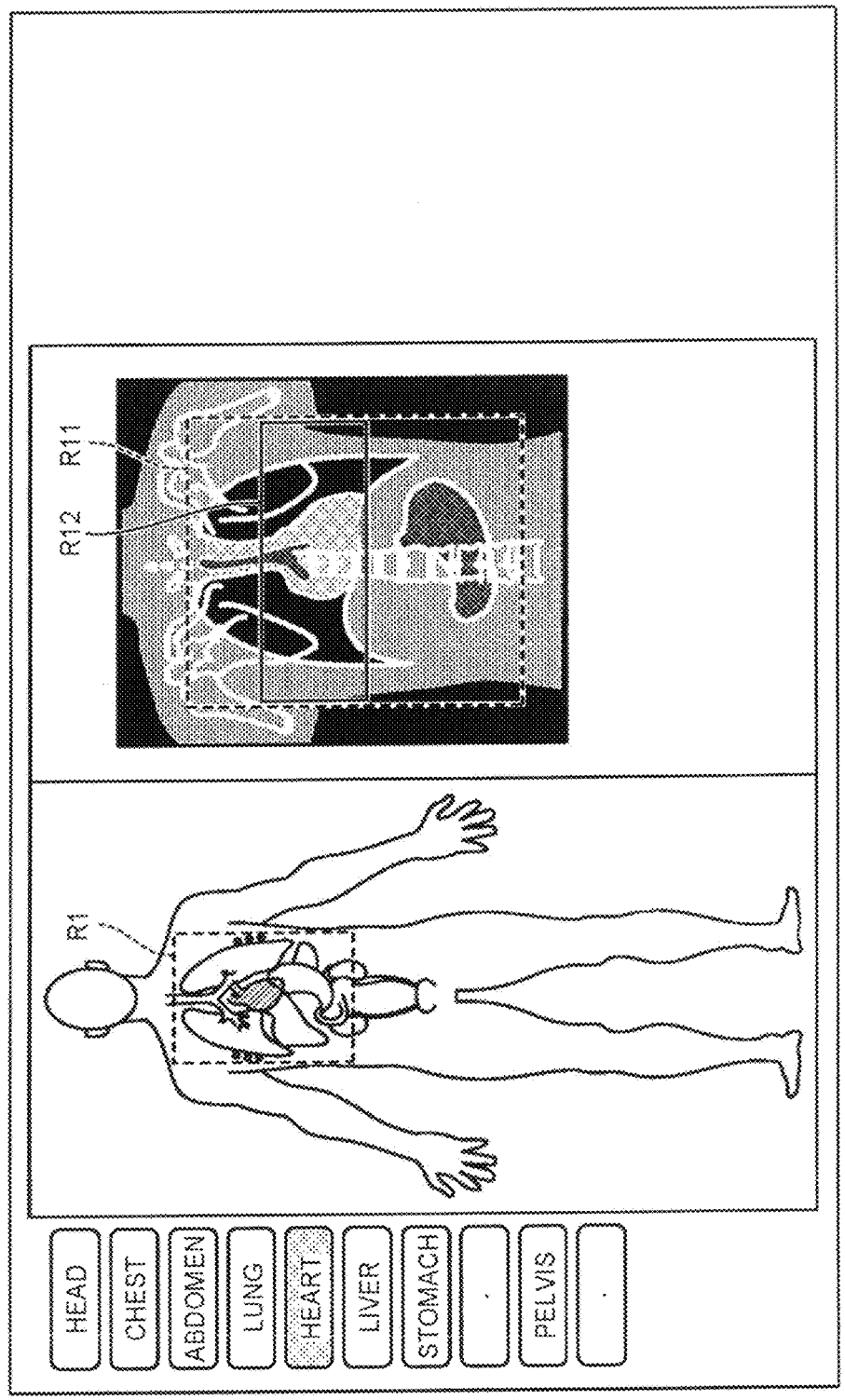

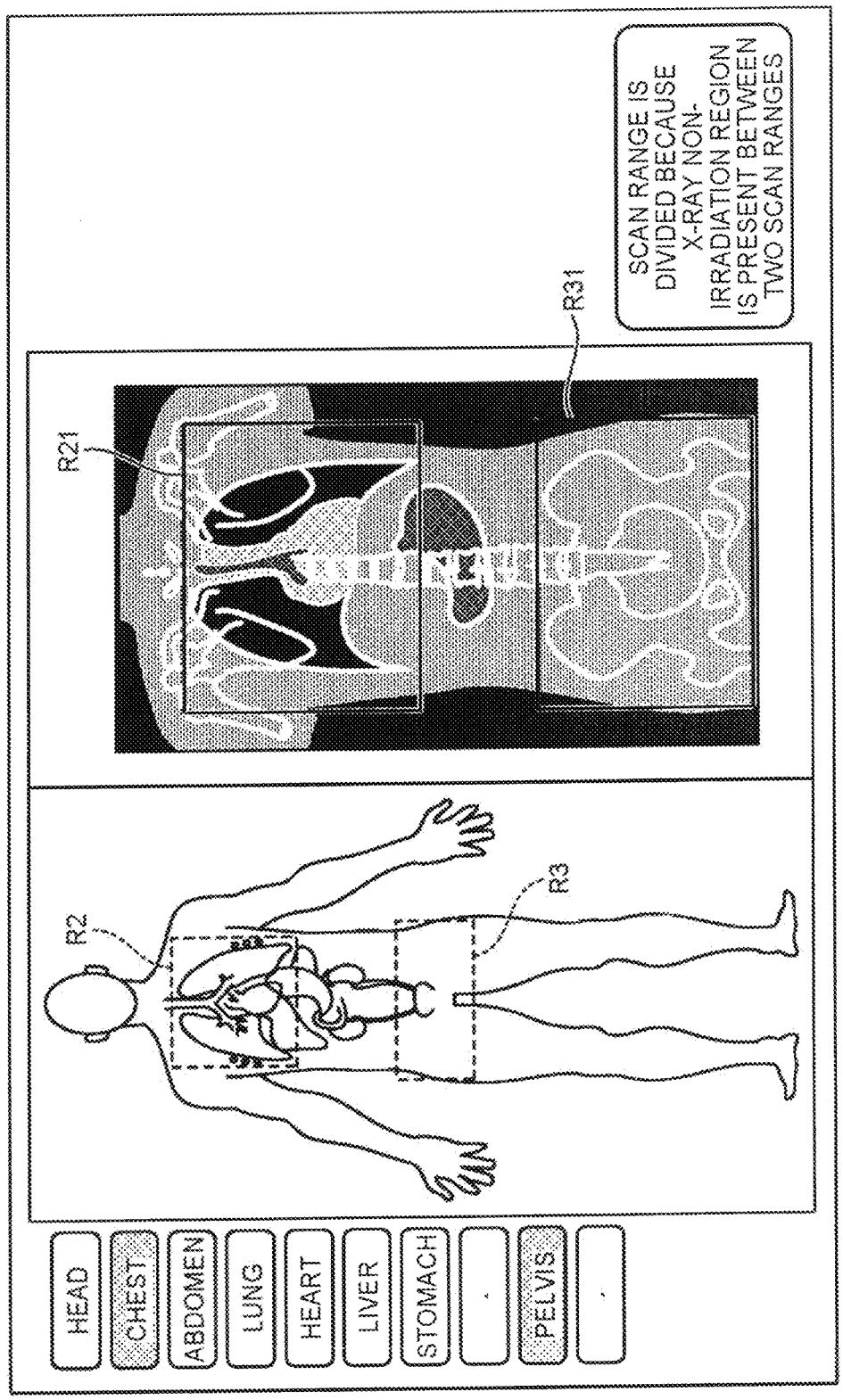

FIG.12

X-RAY COMPUTED-TOMOGRAPHY APPARATUS AND IMAGING-CONDITION-SETTING SUPPORT APPARATUS

CROSS-REFERENCE TO RELATED APPLICATION(S)

This application is based upon and claims the benefit of priority from Japanese Patent Application No. 2014-087764, filed on Apr. 21, 2014, the entire contents of all of which are incorporated herein by reference.

FIELD

Embodiments described herein relate generally to an X-ray computed-tomography (X-ray CT) apparatus and an imaging-condition-setting support apparatus.

BACKGROUND

In CT radioscopy in examination by an X-ray computed-tomography apparatus, improvement of operability, examination precision, and examination throughput are particularly important. So-called protocol preset in which scanning conditions and the like are set at the preliminary planning stage in a conventional X-ray computed-tomography apparatus is made assuming an examined part and examination details; however, it is only rough setting made by numeric value input. However, because the size (body shape) varies for each subject (patient), and because the subject (patient) cannot necessarily be placed in the radiographic center, adjustment of an imaging range is necessary after imaging of a positioning image during examination without exception.

As shown in FIG. 12, when creating protocol presets, a scan start position, a scan end position, an imaging calibration (C)-field of view (FOV), a reconstruction D (display)-FOV (including all of axial, sagittal, coronal, and oblique), and a reconstruction center (X, Y) are input by numeric values. Moreover, as shown in FIG. 13, a scan range and a reconstruction range that have been preset are displayed in figures at the time of performing examination, and are adjusted as necessary. These scan/reconstruction positions, scan/reconstruction ranges, and the like are input roughly by a technician based on his/her experience. However, because those vary for each subject, adjustment of the scan position and reconstruction position and adjustment of the scan range and reconstruction range are performed each time during examination without exception. This process requires much time. Furthermore, because the numeric value input is performed before imaging of a positioning image, it can only planned assuming a position and a range of each part from the body shape, age, and the like of the subject. Therefore, the adjustment therefor requires experience of each technician or the like, and it is hard to understand the plans for an inexperienced operator only from numeric values. Moreover, because adjustment is required eventually, range setting to detail is not possible at the time of planning.

BRIEF DESCRIPTION OF THE DRAWINGS

FIG. 6 is a diagram for supplementary explanation of processing at steps S14 and S15 in FIG. 2;

FIG. 7 is a diagram for supplementary explanation of processing at step S16 in FIG. 2;

FIG. 8 shows one example of changing of a scan position and a scan range according to the present embodiment;

FIG. 9A is a diagram for explaining one example of scan range division according to the present embodiment;

Figure 12:
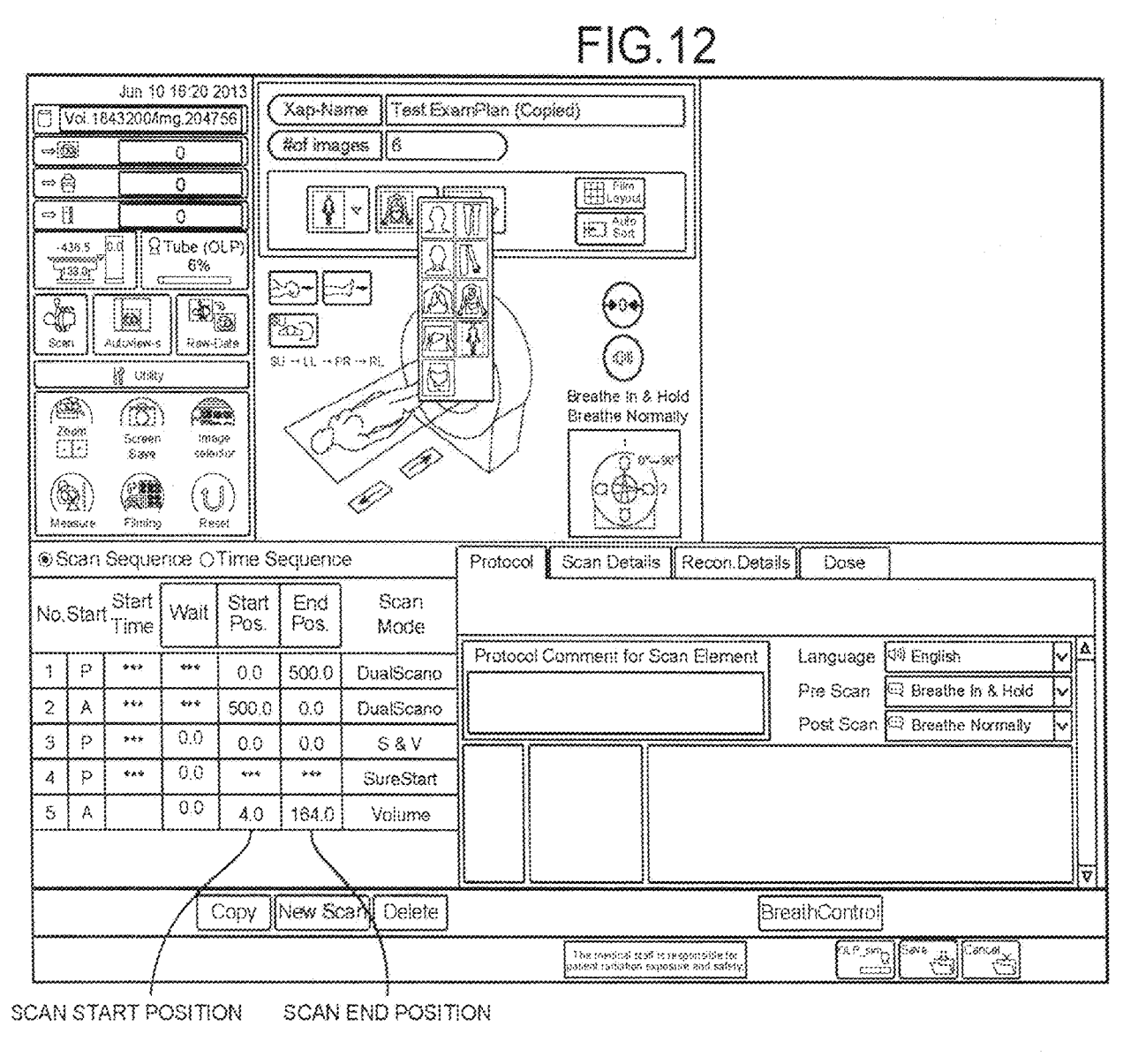

FIG. 12 shows an example of a conventional protocol preset screen, and

DETAILED DESCRIPTION

According to embodiment, an X-ray computed-tomography apparatus includes an X-ray tube, a high-voltage generator, an X-ray detector, a rotation frame and processing circuitry. The X-ray tube generates X-rays. The high-voltage generator configured to generate a tube voltage to be applied to the X-ray tube. The X-ray detector configured to detect an X-ray that is irradiated from the X-ray tube, and that has passed through a subject. The rotation frame configured to support the X-ray tube in a rotatable manner around the subject. The processing circuitry configured to control the high-voltage generating unit and the rotation mechanism to perform positioning scanning and main scanning on the subject. The processing circuitry configured to reconstruct image data based on projection data that is generated by an output of the X-ray detector. The processing circuitry configured to specify any one of a scan position and a scan range for the main scanning. The processing circuitry configured to identify a characteristic point based on a structure inside the subject from the image data, and change any one of the scan position and the scan range specified by the specifying unit, based on a result of checking data relating to the characteristic point and data relating to a corresponding anatomical characteristic point in a virtual subject against each other.

An X-ray computed-tomography apparatus, an imaging-condition-setting support apparatus, and a personal-identification-data generating apparatus according to a present embodiment are explained with reference to the accompanying drawings. The present embodiment is achieved for the purpose of enhancing the accuracy of preset for an imaging position, an imaging range, and the like in a stage prior to imaging a positioning image, thereby improving a workflow of an examination procedure (examination protocol) from the preset to execution of examination, and increasing examination throughput, and is targeted to imaging-condition-setting support apparatuses and further to medical imaging apparatuses that includes the imaging-condition-setting support apparatus. Explanation is given herein with an X-ray computed-tomography apparatus as an example. An important point of the imaging-condition-setting support apparatus is that anatomical characteristics (anatomical landmarks) on an image of a virtual average subject (virtual patient image) and characteristics (for example, anatomical characteristics, and the like) based on structures inside a subject on an image that is acquired by imaging the subject are naturally in correspondence in anatomical terms, and using technical characteristics that a positional gap between points of the same anatomical characteristics is identified, it can be achieved to complete preset for an imaging position and the like on the virtual patient image.

Figure 1:
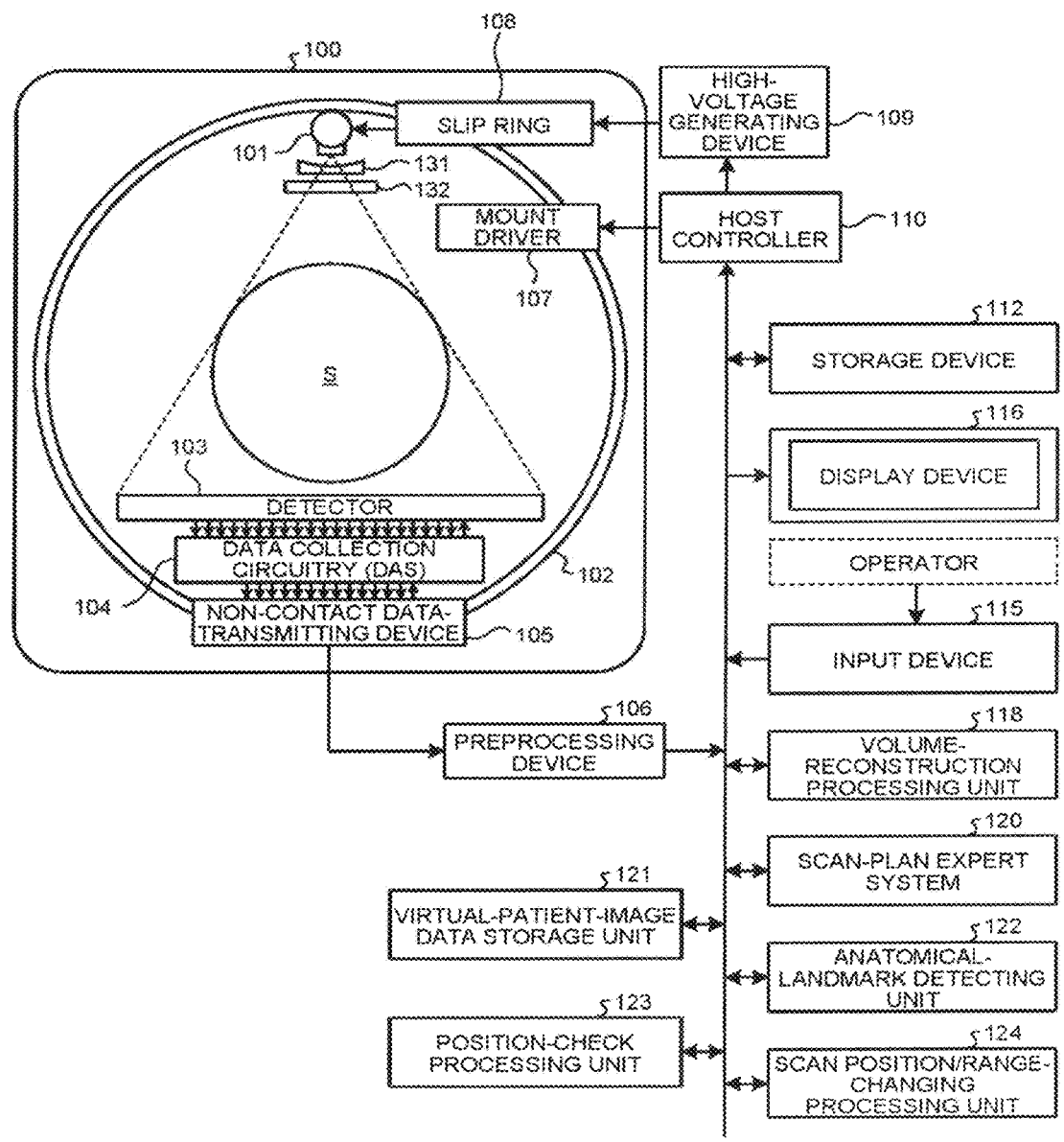
FIG. 1 shows a configuration of an X-ray computed-tomography apparatus according to a present embodiment.

FIG. 1 shows a configuration of the X-ray computed-tomography apparatus according to the present embodiment. A medical imaging apparatus includes various kinds of apparatuses that generates images relating to a subject such as an X-ray diagnosis apparatus, an X-ray computed-tomography apparatus, a magnetic-resonance imaging apparatus (MRI), an ultrasonography apparatus, and a gamma camera, and the present embodiment is applicable to any of those. An X-ray computed-tomography apparatus is explained herein as an example of the medical imaging apparatus. Moreover, there are various types of the X-ray computed-tomography apparatus, such as a rotate/rotate type in which an X-ray tube and a radiation detector are integrated into one unit and rotate around a subject, and one of a stationary/rotate type in which a large number of detection devices are arrayed in a ring shape and only an X-ray tube rotates around a subject, and the present embodiment is applicable to any type. Herein, the rotate/rotate type currently dominating is explained. Furthermore, to reconstruct a tomographic image of one slice, projection data for 360° around the circumference of a subject is required, and projection data for 180°+a view angle is required even in a half scan method. The present embodiment is applicable to either of the reconstruction methods. Furthermore, as for the mechanism of converting incident X-rays into electric charges, an indirect conversion in which X-rays are converted into light by a fluorescent material such as a scintillator, and the light is further converted into electric charges by a photoelectric transducer such as a photodiode, and a direct conversion in which generation of an electron positive-hole pair by X-rays inside a semiconductor and movement thereof to an electrode, that is, a photoconduction phenomenon is applied are mainstream. As an X-ray detection device, either method can be applied; however, the former indirect conversion is explained herein. Moreover, in recent years, commercialization of a so-called multi-tube X-ray computed-tomography apparatus that are equipped with multiple pairs of an X-ray tube and an X-ray detector on a rotation ring has been advanced, and development of peripheral technology thereof has been advanced. The present embodiment is applicable to either a conventional one-tube X-ray computed-tomography apparatus or the multi-tube X-ray computed-tomography apparatus. Herein, apparatus of a one-tube type is explained.

FIG. 1 shows a configuration of an essential part of the X-ray computed-tomography apparatus according to the present embodiment. The X-ray computed-tomography apparatus of the present embodiment includes a gantry 100. The gantry 100 includes a tubular rotation frame 102. The rotation frame 102 is driven by a mount driver 107, and rotates about a rotation axis RA as a center. On this rotation frame 102, an X-ray tube 101 and an X-ray detector 103 are mounted opposing to each other. The X-ray tube 101 receives application of a tube voltage and supply of a filament current through a slip ring 108, and generates X-rays. The X-ray detector 103 detects X-rays that have passed through a subject, and outputs an electric signal that reflects a dose of incident X-ray. The signal (referred to as real raw data) output from the X-ray detector 103 is supplied to a preprocessing device 106 through a data collection circuitry 104 and a non-contact data-transmitting device 105. The data (referred to as projection data or raw data) subjected to processing such as sensitivity correction and logarithmic conversion in the preprocessing device 106 is stored in a storage device 112.

In the gantry 100, as shown in FIG. 1, a bow-tie filter 131 and a collimator 132 are arranged between the X-ray tube 101 and the X-ray detector 103. The bow-tie filter 131 is an X-ray filter to adjust an X-ray dose of X-rays emitted from the X-ray tube 101. Specifically, the bow-tie filter 131 is a filter that has X-rays emitted from the X-ray tube 101 pass therethrough and attenuate so that X-rays irradiated to a subject P from the X-ray tube 101 have a predetermined distribution. For example, the bow-tie filter 131 is a filter that is made by processing aluminum so as to have a predetermined target angle and a predetermined thickness. The collimator 132 is a slit to narrow an irradiation range of the X-rays the dose of which has been adjusted by the bow-tie filter 131.

A host controller 110 performs overall control of the X-ray computed-tomography apparatus. For example, the host controller 110 controls respective operations of the mount driver 107, a high-voltage generating device 109, and the like to collect data (scan). Moreover, the host controller 110 controls operation based on various instructions that are input through an input device 115 and display processing of various kinds of information of a display device 116. Furthermore, the host controller 110 controls various kinds of processing performed by respective components by controlling respective components included in the X-ray computed-tomography apparatus.

A volume-reconstruction processing unit 118 reconstructs volume data or two-dimensional tomographic-image data based on projection data that is stored in the storage device 112. The volume data and the two-dimensional tomographic-image data are collectively called "image". The display device 116 is provided to display image data, and to display an operation screen by a scan-plan expert system 120. The input device 115 is constituted of a keyboard, a mouse, and the like to input instructions from an operator.

A virtual-patient-image data storage unit 121 stores data of multiple virtual patient images respectively corresponding to multiple combinations of parameters relating to age, adult/child, male/female, a body shape such as weight and height, and the like in advance. The virtual patient image is prepared in advance as an image that is obtained by actually imaging, by X-rays, a human body that has an average body shape and the like according to a combination of the above parameters corresponding thereto. Human bodies have many anatomical characteristics that can be extracted relatively easily from an image based on the structural characteristics and the like, by image processing such as pattern recognition. The position or arrangement in a body of these many anatomical characteristic points are roughly invariable according to age, adult/child, male/female, a body shape such as weight and height, and the like. These many anatomical characteristic points are detected in advance in each virtual patient image, and position data thereof is stored annexing to or associating with data of the virtual patient image together with an identification code of each anatomical characteristic.

The scan-plan expert system 120 is a system that is constructed to support setting of a scan plan (also referred to as scan protocol) mainly. Multiple scan protocol candidates are determined according to age, adult/child, male/female, a body shape such as weight and height, a purpose of examination, and the like, and the scan-plan expert system 120 provides these scan protocol candidates to a user, and extracts items such as age, adult/child, male/female, weight, height, and the like from subject data, and selects one virtual patient image from the virtual patient images stored in the virtual-patient-image data storage unit 121 according to these items. The scan candidate includes recommended values of an imaging range of a positioning image, an imaging angle of a positioning image, a tube voltage and a tube current for imaging a positioning image, a scan mode of main scanning, a scan position, a scan range, a tube voltage and a tube current for main scanning, and the like. The virtual patient image is displayed on a scan-protocol-setting support screen as exemplified in FIG. 3. On the virtual patient image on the scan-protocol-setting support screen, additional frames and additional lines indicating a scan position, a scan range, a reconstruction position, and a reconstruction range are superimposed. Alternatively, a specified organ (district) is displayed (in an enhanced manner). Initial positions, ranges, of the additional frames and the additional lines on a virtual patient image, and a specified organ (district) are determined according to a scan protocol. A user operates the additional frames and the additional lines arbitrarily through the input device 115, to adjust the scan position and the scan range. It is not necessarily made by operating the additional frames and additional lines, but also made by specifying numeric values, and scan range and position are specified by a width in a scanning diameter direction (C-FOV), and a scan range (position) in a body axis direction relative to a subject, and specification of reconstruction range and position may be made by specifying a width and a center (a D-FOV and a reconstruction center) in a diameter direction of reconstruction of each of images of axial/sagittal/coronal, and a range thereof.

When a scan protocol is determined, data of a scan position, a scan range, a reconstruction position, a reconstruction range, and the like relating to the scan protocol are stored in an internal storage unit of the scan-plan expert system 120.

An anatomical-landmark detecting unit 122 extracts multiple anatomical characteristic points from a positioning image that is acquired by imaging a subject at the beginning of this scan sequence based on structural characteristics and the like by image processing such as pattern recognition. Position data of each anatomical characteristic point is held in the internal storage unit together with the identification code of each of the anatomical characteristics. Furthermore, the anatomical-landmark detecting unit 122 can extract multiple anatomical characteristic points also from image data that is acquired by main scanning based on structural characteristics by image processing such as pattern recognition.

A position-check processing unit 123 performs position checking between anatomical characteristic points on a virtual patient image that is included in each of a scan position, a scan range, a reconstruction position, and a reconstruction range of a preset scan protocol and anatomical characteristic points that are extracted from a positioning image associated with the same identification code as these anatomical characteristic points on the virtual patient image, and associates with each other. Based on a result of the checking, a scan position/range-changing processing unit 124 changes a scan range and the like specified on the virtual patient image into a scan range and the like on a positioning image that defines the anatomically same position and range. In brief, a scan range, reconstruction range, and the like on a positioning image are determined so that all of anatomical characteristic points on the positioning image that correspond to the anatomical characteristic points included in a scan range that is specified on a virtual patient image are included therein. Details are described later. The host controller 110 controls the respective components 107 and 109 so that scan is performed according to the scan range and the like on the positioning image thus changed.

When a human body is inserted obliquely relative to a scanner, it is arranged so that a reconstruction range is planned parallel and perpendicularly relative to the human body. Attention is called to a fact that a human body is inserted obliquely relative to the scanner and a reconstruction range anatomically planned is not parallel and perpendicular relative to an actual human body in a message, and it is encouraged to correct the angle of the reconstruction range anatomically planned on the positioning image to be planned so that the reconstruction range is parallel and perpendicular relative to the human body. At this time, based on anatomically planned reconstruction data and body axis data, axial, coronal, and sagittal images are formed on oblique sections that are inclined relative to the rotation axis in an actual state (three perpendicular sections of a human body although images have not been able to be formed on three sections perpendicular to each other on scanner view conventionally). Moreover, the scan range is automatically adjusted to be extended so as to include the reconstruction range anatomically planned.

Furthermore, not only the range, but also a scan condition, and a reconstruction condition are automatically set referring to data preset for each classified part. Not only the scan range, but also a tube current, milliampere (mA), an tube voltage, kilovolt (kV) are also automatically determined as a scan condition according to a part so that an SD, an image thickness, a reconstruction function, and the like preset for each part are realized.

In the present embodiment, because an organ of a subject can be identified in three dimensions, it is possible to narrow the aperture of the collimator 132 so as to irradiate an X-ray only on a subject organ to achieve reduction of radiation exposure. Furthermore, it is possible to change the aperture of the collimator 132 for every angle of an X-ray tube according to a three-dimensional shape of a subject organ, and to change the aperture of the collimator 132 according to a position on a Z axis (body axis, rotation axis). Moreover, when a subject organ is far away from a rotation center, or the like, it is also possible to adjust a position of a bed top panel vertically and horizontally so that a center of the subject organ matches with, or comes close to the rotation center.

When a positioning image is not imaged, it is possible to estimate a position of a subject organ roughly based on input height, weight, and sex, and to provide candidates of a scan range and a reconstruction range. A scan condition and a reconstruction condition are provided maintaining the preset data. When helical scan is performed, analysis of anatomical landmarks is performed based on three-dimensional data thereof, to enhance the accuracy in setting of a scan condition and a reconstruction condition.

Figure 2:
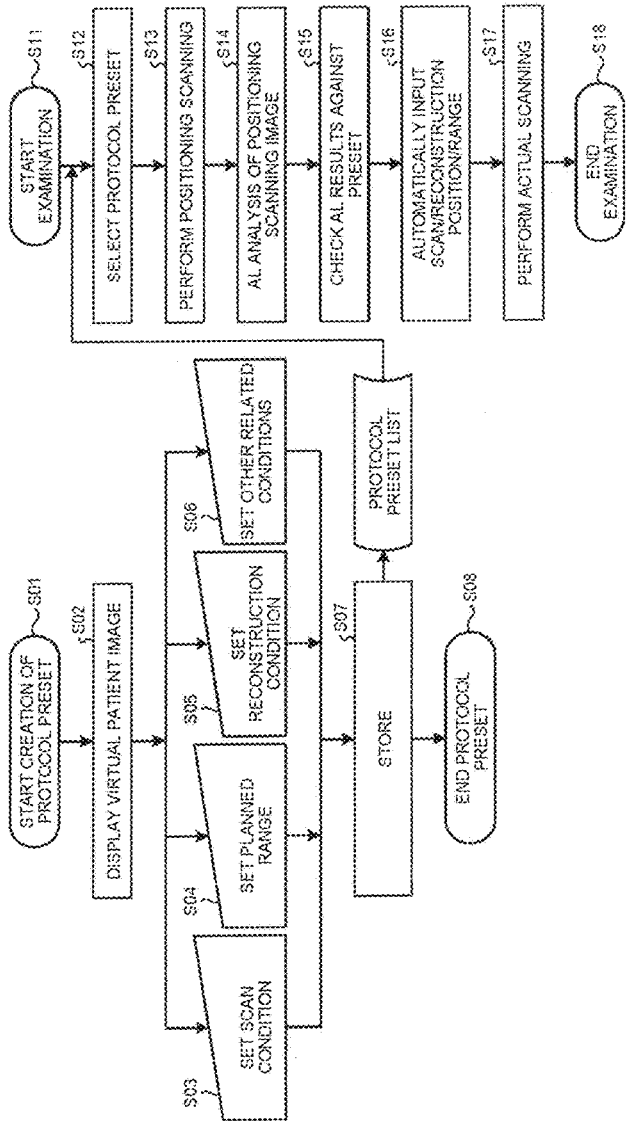
FIG. 2 is a flowchart indicating a protocol-preset processing procedure and examination processing procedure according to the present embodiment.

FIG. 2 indicates a processing procedure in the present embodiment. Steps S01 to S08 indicate steps in a preset stage, and steps S11 to S18 indicate steps in a main scanning stage. Preset creation processing is started by the scan-plan expert system 120 in a stage prior to imaging of a positioning image (S01). The preset creation processing can be performed at the time when an examination request is issued, and it is not necessary to wait until a positioning image of a subject is imaged as a conventional case.

Figure 3:
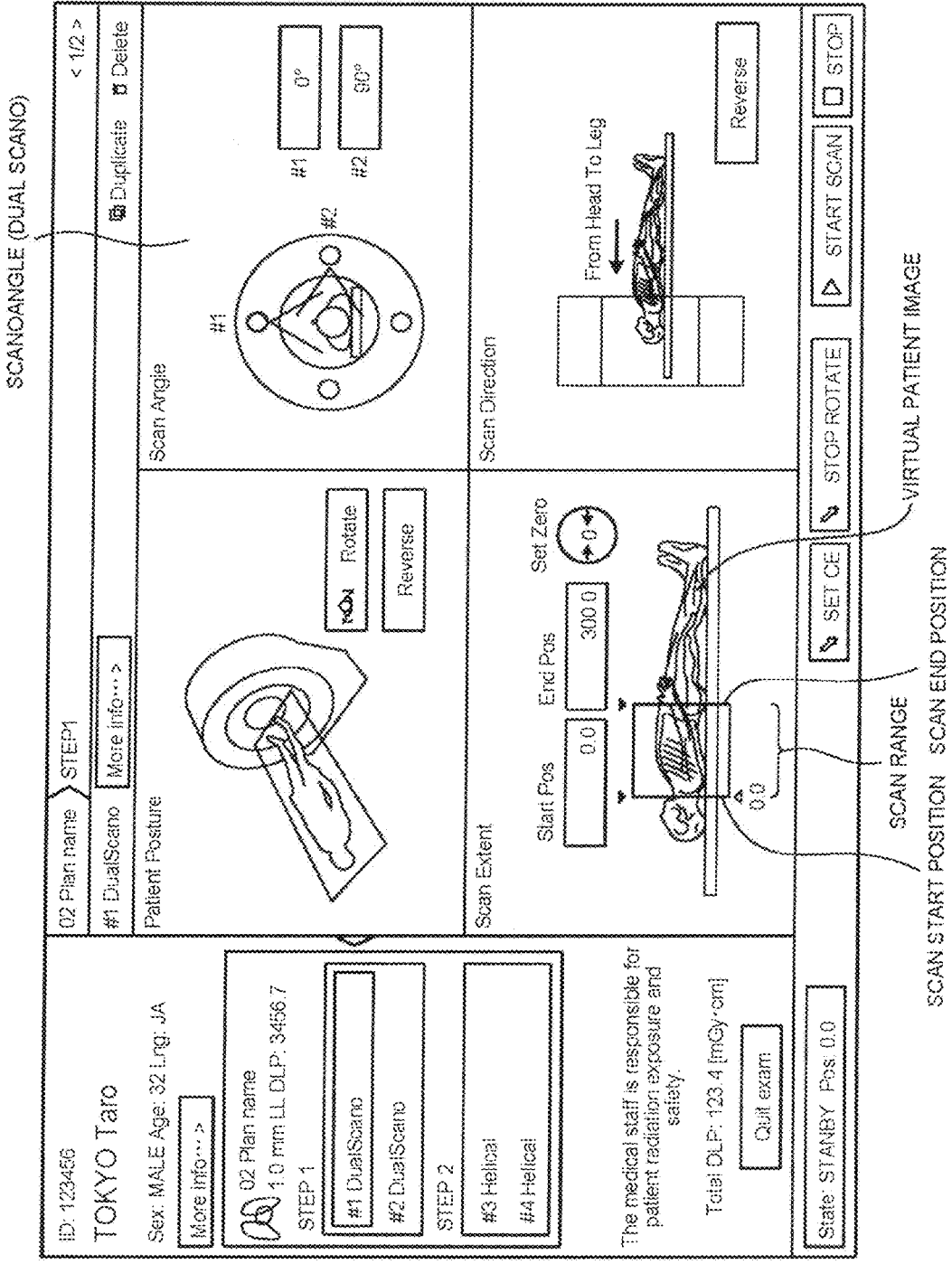
FIG. 3 shows an example of an input screen at steps S03 to S06 in FIG. 2.

First, the scan-plan expert system 120 extracts items such as age, adult/child, male/female, weight, height, and the like from subject data that is included in the examination request data, and according to these items, one piece of the virtual patient image that is most relevant with the subject is selected and read from the virtual-patient-image data storage unit 121, and is displayed on the display device 116 (S02). The virtual patient image is included in a scan-protocol-setting support screen as shown in FIG. 3. This scan-protocol-setting support screen shown in FIG. 3 indicates an example of a scan protocol in which a positioning image is imaged from two directions and helical scanning is performed on a chest. In the virtual patient image on the scan-protocol-setting support screen, a scan start position, a scan end position, and a scan range are indicated by additional lines and additional frames. These additional lines and additional frames indicating a scan start position, a scan end position, and a scan range are initially displayed at recommended positions and recommended range that are included in advance in the scan protocol. A user adjusts the scan position and the scan range by arbitrarily operating the additional lines and the additional frames through the input device 115. Thus, a planned range is set (S04). At presetting, scan conditions such as a tube voltage, a tube current, and a scan time are set in addition to a planned range such as a scan position and a scan range (S03), reconstruction conditions such as a reconstruction position, a reconstruction range, and a choice of reconstruction function are set (S05), and further, as an amount of a contrast agent to be injected by an injector and a sequence thereof, and other conditions such as a time interval between scans are set (S06). These sets of condition data are referred to as protocol preset data. This protocol preset data is stored in the internal storage unit of the scan-plan expert system 120 (S07).

Next, processing procedure (S11 to S18) in the main scanning stage is explained. A list relating to multiple protocol presets corresponding to multiple examination requests that have not been executed are read from the internal storage unit of the scan-plan expert system 120, to be displayed on the display device 116. A protocol preset for an examination that is to be executed is selected according to an instruction from a user (S12). Positioning scanning, that is imaging (in one direction, two directions, and helical 3D) of a positioning image in the protocol preset is performed (S13). In this example, front imaging is performed from a position of the X-ray tube 101 at 0°, and side imaging is performed from a position at 90°.

Figure 4:
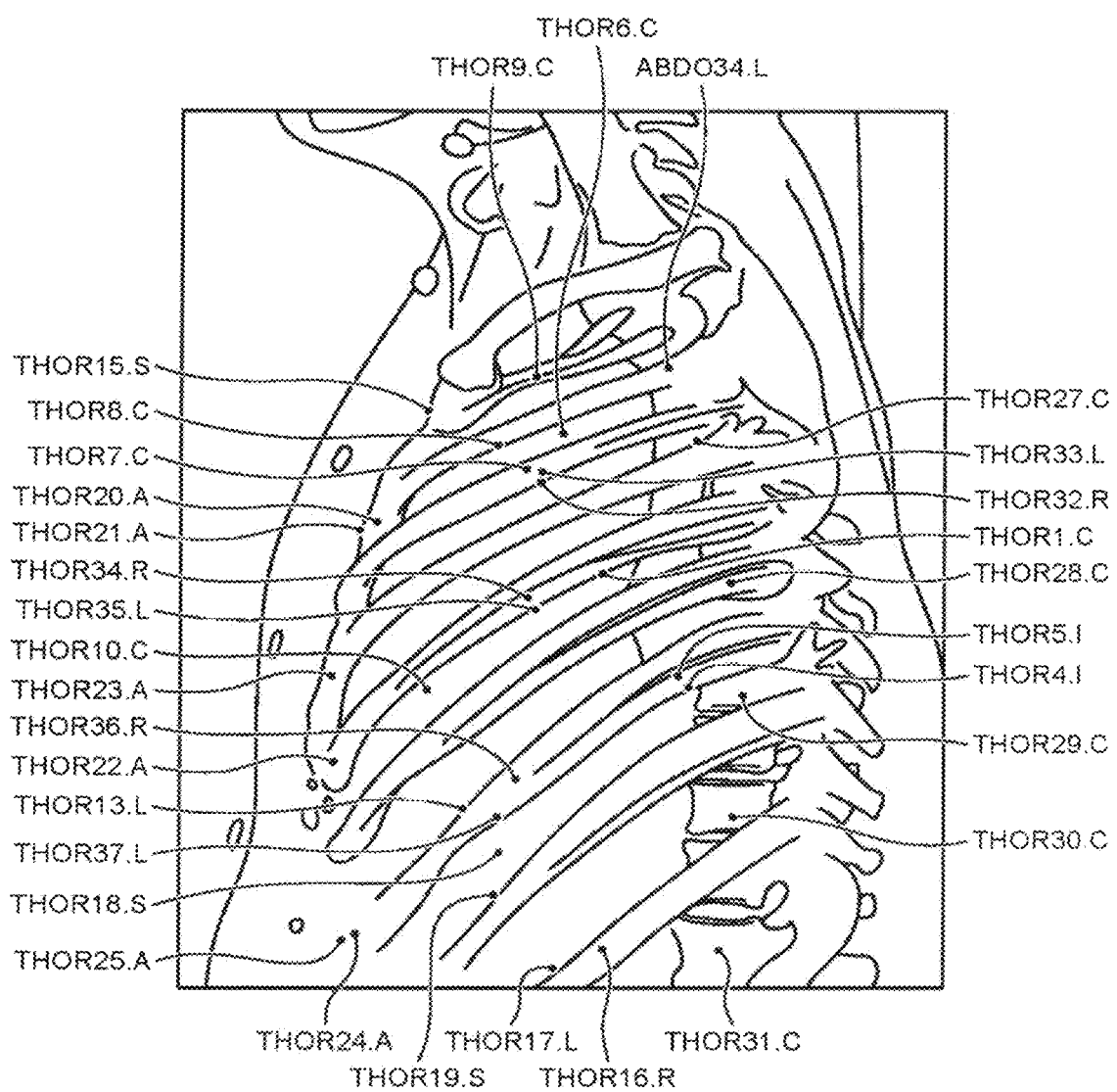
FIG. 4 shows one example of anatomical characteristics specified at step S14 in FIG. 2.
Figure 5:
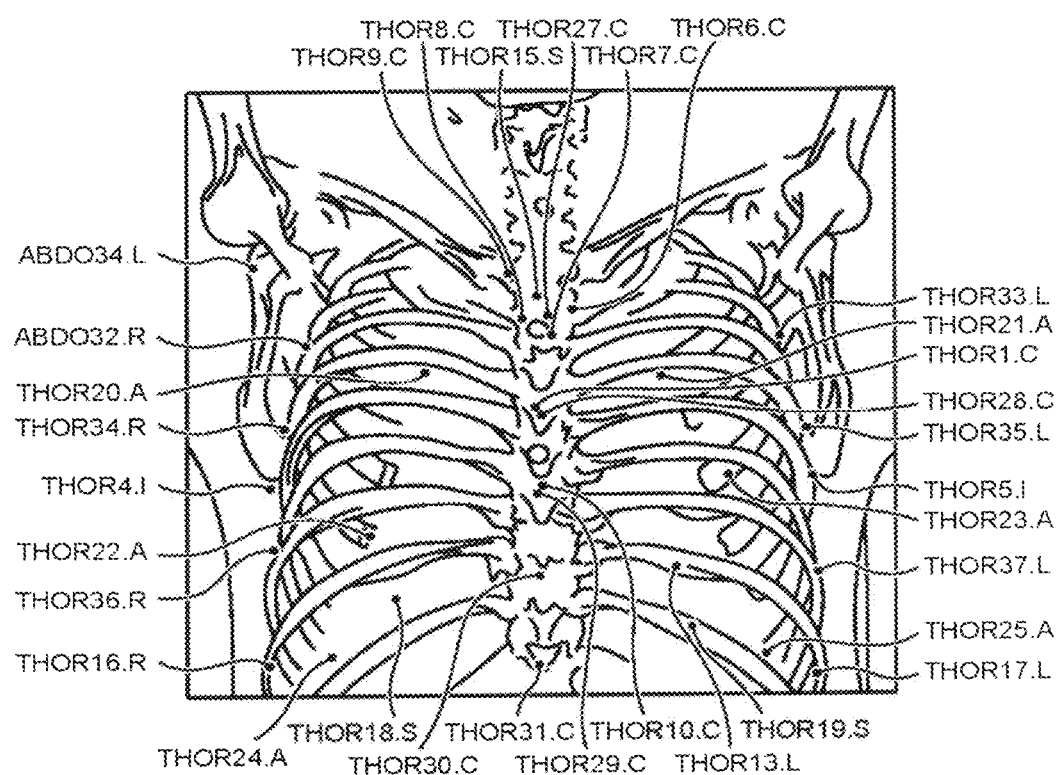
FIG. 5 shows one example of anatomical characteristics specified at step S14 in FIG. 2.

Subsequently, the positioning image is subjected to analysis processing by the anatomical-landmark detecting unit 122, and multiple anatomical characteristic points that are scattered on the positioning image are extracted as exemplified in FIG. 4 and FIG. 5 (S14). In FIG. 4 and FIG. 5, an identification code of anatomical characteristic is assigned to each point according to each anatomical position. For example, THOR6.C and so on indicates the identification code of anatomical characteristic. According to this identification code of anatomical characteristic, position check by the position-check processing unit 123 is performed as shown in FIG. 6. That is, anatomical characteristic points ALC01 to ALCn that are extracted from the positioning image and that are associated with the same identification codes as those of anatomical characteristic points ALV01 to ALVn on the virtual patient image in the scan range of the preset scan protocol are identified (S15).

Based on this result of position checking, a scan range SRC on the positioning image that indicates an anatomical range same as a scan range SRV specified on the virtual patient image is set (step S16). That is, as shown in FIG. 6, the anatomical characteristic points ALV01 to ALVn included in the scan range SRV that is specified on the virtual patient image are identified, and the scan range SRV is changed into a scan range SRC in such a manner that the anatomical characteristic points ALC01 to ALCn on the positioning image that correspond to the anatomical characteristic points ALV01 to ALVn are included therein. Specifically, as shown in FIG. 7, a coordinate conversion matrix H is acquired so that a total of positional gaps among anatomical characteristic points (ALN01, ALC01), (ALN02, ALC02), and (ALN03, ALC03) that are anatomically the same is minimized.

$$LS=((X1,Y1,Z1)-H(x1,y1,z1))+((X2,Y2,Z2)-H(x2,y2,z2))+((X3,Y3,Z3)-H(x3,y3,z3))$$

By the acquired coordinate transformation matrix H, the scan range SRV specified on the virtual patient image is changed into the scan range SRC on the positioning image (S16). The main scanning is performed according to this scan range SRC (S17).

As described, according to the present embodiment, the virtual patient image is displayed for range specification at the time of preset and a position and a range are planned thereon, and after imaging a positioning image (image for determining a scan position and a range) for performing examination, a scan rage can be set by setting numeric values according to a range that is automatically planned from the positioning image. This can be achieved by applying a technology of automatic extraction of anatomical landmarks (AL) using the positioning image and by checking extracted AL and the positioning image against each other.

That is, according to the present embodiment, a workflow at the time of performing examination is changed from that at the time of protocol preset, and a scan range and the like are set in advance using the virtual patient image, and are changed into a scan range and the like on the positioning image of an actual subject according to a result of checking anatomical characteristic points, thereby achieving improvement of the accuracy of preset and increase of throughput. The frequency and the work load of resetting and adjusting, after imaging a positioning image, a scan position, a scan range, a reconstruction position, a reconstruction range, and the like that have been set at the protocol preset can be eliminated or reduced. Moreover, because automation of scan range setting is achieved, it is possible to provide a means to perform a reliable examination even by an inexperienced operator at emergency and the like.

When a positioning image is not present or cannot be acquired at the time of examination, it can be handled by automatically inputting estimated range and position by numeric values based on part data that is registered in a selected protocol preset, and then by having a user adjust manually. Alternatively, a means to input numeric values similarly to a current state is also supported, and values thereof are used. Furthermore, when anatomical characteristic points are not detected precisely also, the same operation is performed as the above case in which a positioning image is not present.

As described above, the X-ray computed-tomography apparatus according to the present embodiment improves the accuracy of preset for an imaging position and the like by changing a specified scan position or the scan range based on a result of checking anatomical characteristic points in a virtual patient image and characteristic points based on a structure inside a subject in image data that is acquired by imaging by positioning scanning or main scanning. In the following, a use example of the X-ray computed-tomography apparatus according to the present embodiment is explained.

For example, in the embodiment described above, a case in which a scan position or a scan range are specified on a virtual patient image, and the specified scan position or scan range are changed into a position or a range on a positioning image, and main scanning is performed in the changed position or range has been explained. However, embodiments are not limited thereto, and a scan position or a scan range specified on image data may be changed to a position or a range on a virtual patient image. That is, the computed tomography apparatus according to a present example can perform a first change in which a position or a range on a virtual patient image is changed to a position or a range on image data, and a second change in which a position or a range on image data is changed to a position or a range on a virtual patient image.

In the following, an example of changing of a scan position and a scan range is explained using FIG. 8. FIG. 8 shows one example of changing of a scan position and a scan range according to the present embodiment. In FIG. 8, one example of graphical user interface (GUI) that is displayed by the display device 116 when a scan position or a scan range is specified after a positioning image is imaged. Specification of a scan position or a scan range described later may be performed according to specification made by an operator thorough the GUI, or may be performed, for example, based on request data from an examination-request data system such as a radiology information system (RIS). That is, the host controller 110 controls to specify a scan position and a scan range specified by an operator through the input device 115. Alternatively, the host controller 110 controls to specify a scan position and a scan range based on data of examination details or a scan subject part included in an examination request for a subject that is received from the examination-request data system connected through a not shown network.

For example, on the GUI that is displayed when a scan position or a scan range is specified, as shown in FIG. 8, buttons to specify a subject part (for example, buttons of head, chest, abdomen, lung, heart, and the like) on a left end, a virtual patient image showing an entire human body, a positioning image that is acquired by positioning scanning are displayed. For example, when a scan range R1 is set on a virtual patient image by an operator operating the input device 115, the host controller 110 outputs coordinate data of the scan range R1 on the virtual patient image to the scan position/range-changing processing unit 124. The scan position/range-changing processing unit 124 sets a scan range R11 by changing the coordinate data of the scan range R1 accepted from the host controller 110 into coordinate data of a positioning image using a coordinate transformation matrix acquired by the position-check processing unit 123.

Moreover, for example, when an operator operates the input device 115 to press a button to specify a subject part, or when a part is specified (selected) in a virtual patient image, the host controller 110 outputs data of a range corresponding to a part of the pressed button, or a range corresponding to the specified part to the scan position/range-changing processing unit 124. Ranges corresponding to parts can be arbitrarily determined at each facility in which the X-ray computed-tomography apparatus is used. As one example, when a scan subject part is heart, in a facility A, a range in which an upper end and a lower end of a heart in a body axis direction are scan start line and a scan end line, respectively is set as a range corresponding to heart. On the other hand, in a facility B, a range in which a position "5 centimeters (cm)" above from an upper end of a heart is a scan start line and a position "5 cm" below from a lower end of to heart in a body axis direction is a scan end line is set as a range corresponding to a heart. Such correspondence information between parts and ranges is stored in the storage device 112 in advance, and when a part is specified, the host controller 110 extracts coordinates of the specified part include in a virtual patient image, and generates coordinate data based on corresponding data to output to the scan position/range-changing processing unit 124. The scan position/range-changing processing unit 124 changes the accepted coordinate data into coordinate data on a positioning image using the coordinate transformation matrix, and thereby sets, for example, a scan range R12 to scan a heart as shown in FIG. 8.

In the example described above, an example in which a range corresponding to a scan subject part is varied per facility has been explained. In the following, a case in which a scan range in main scanning is varied according to a scan time is explained. In such a case, for example, a scan range may be varied according to breath of a subject. As one example, according to a time period for which the breath can be held, a scan range is set per subject. That is, for a subject the breath holding time of which is long, a scan range is set large, and for a subject the breath holding time of which is short, a scan range is set small. For example, scan possible time is set per subject, and when scan of a chest that is likely to be influenced by breathing is performed, the host controller 110 sets a scan range according to the scan possible time corresponding to a subject.

Although a case in which an operation specifies a part through the input device 115 has been explained in the example described above, a scan range for main scanning can be set by using data of an examination request (disease data, and the like), similarly. In such a case, the host controller 110 extracts a part to be a scan subject, reads correspondence data that corresponds to the extracted part from the storage device 112, and generates coordinate data from coordinates of the extracted part on a virtual patient image and the correspondence data to output to the scan position/range-changing processing unit 124.

Furthermore, a case in which a range is not changed in a Y axis direction (the horizontal direction in the drawing) even when heart is the scan subject part has been explained in the example shown in FIG. 8. However, embodiments are not limited thereto, and a range may be changed also in the Y axis direction according to a scan subject part. As one example, when a heart is a scan subject part, the host controller 110 changes a range in the Y axis direction so that the range is the minimum range including the heart in the Y axis direction. The host controller 110 sets the "C-FOV" according to a scan range in the Y axis direction by controlling the bow-tie filter 131 or the collimator 132. That is, the host controller 110 sets the "C-FOV" that includes the range in the Y axis direction and is in a minimum size.

In the example described above, a case in which a specified scan position or scan range is just one has been explained. However, in diagnostic imaging using an X-ray computed-tomography apparatus, there is a case in which more than one part is specified in multiple single scan sequences. When more than one scan position or scan range is specified, the X-ray computed-tomography apparatus according to the present application divides or unifies a scan range based on positional relation of X-ray irradiation ranges to scan the respective scan subject parts. Specifically, the host controller 110 controls the scan position/range-changing processing unit 124 to divide a scan range, when X-ray irradiation regions to scan the respective scan subject parts are distant from each other, so that each of the scan subject parts is independently scanned, and to unify scan ranges, when X-ray irradiation regions to scan the respective scan subject parts are overlapped with each other, so that the respective scan subject parts are collectively scanned.

FIG. 9A is a diagram for explaining one example of scan range division according to the present embodiment. For example, as shown in FIG. 9A, when a "chest" and a "pelvis" are specified as scan subject parts, the scan position/range-changing processing unit 124 changes coordinate data of a scan range R2 corresponding to a "chest" on a virtual patient image into coordinate data of a scan range R21 in image data. Furthermore, the scan position/range-changing processing unit 124 convers coordinate data of a scan range R3 corresponding to a "pelvis" on the virtual patient image into coordinate data of a scan range R31 in the image data.

Subsequently, the scan position/range-changing processing unit 124 determines whether X-ray irradiation regions overlap with each other when the scan range R21 and the scan range R31 are scanned, and have the respective scan ranges scanned independently by setting the respective scan ranges as they are when determining that the X-ray irradiation regions do not overlap with each other. The X-ray irradiation regions when the scan range R21 and the scan range R31 are scanned are not only the scan ranges illustrated, but margins for scanning are generated at an upper end and a lower end of the respective ranges in a body axis direction (the vertical direction in the drawing). That is, the regions in which X-rays are actually irradiated on the subject are not only the scan range R21 and the scan range R31, but includes X-ray irradiation regions at both the upper end and the lower end in the body axis direction. The scan position/range-changing processing unit 124 determines whether X-ray irradiation regions overlap with each other including the margins described above when determining whether X-ray irradiation regions overlap with each other at scanning the scan range R21 and the scan range R31.

When determining that the X-ray irradiation regions to scan the respective scan ranges do not overlap with each other including the margins, the scan position/range-changing processing unit 124 sets the scan range R21 and the scan range R31 for main scanning as shown in FIG. 9A. Thus, unnecessary radiation exposure can be avoided. When the scan ranges are set by the scan position/range-changing processing unit 124, the host controller 110 controls to display, on the display device 116, a result of scan range setting as "SCAN RANGE IS DIVIDED BECAUSE X-RAY NON-IRRADIATION REGION IS PRESENT BETWEEN TWO SCAN RANGES" as shown in FIG. 9A, together with a reason for the setting.

Figure 9B:
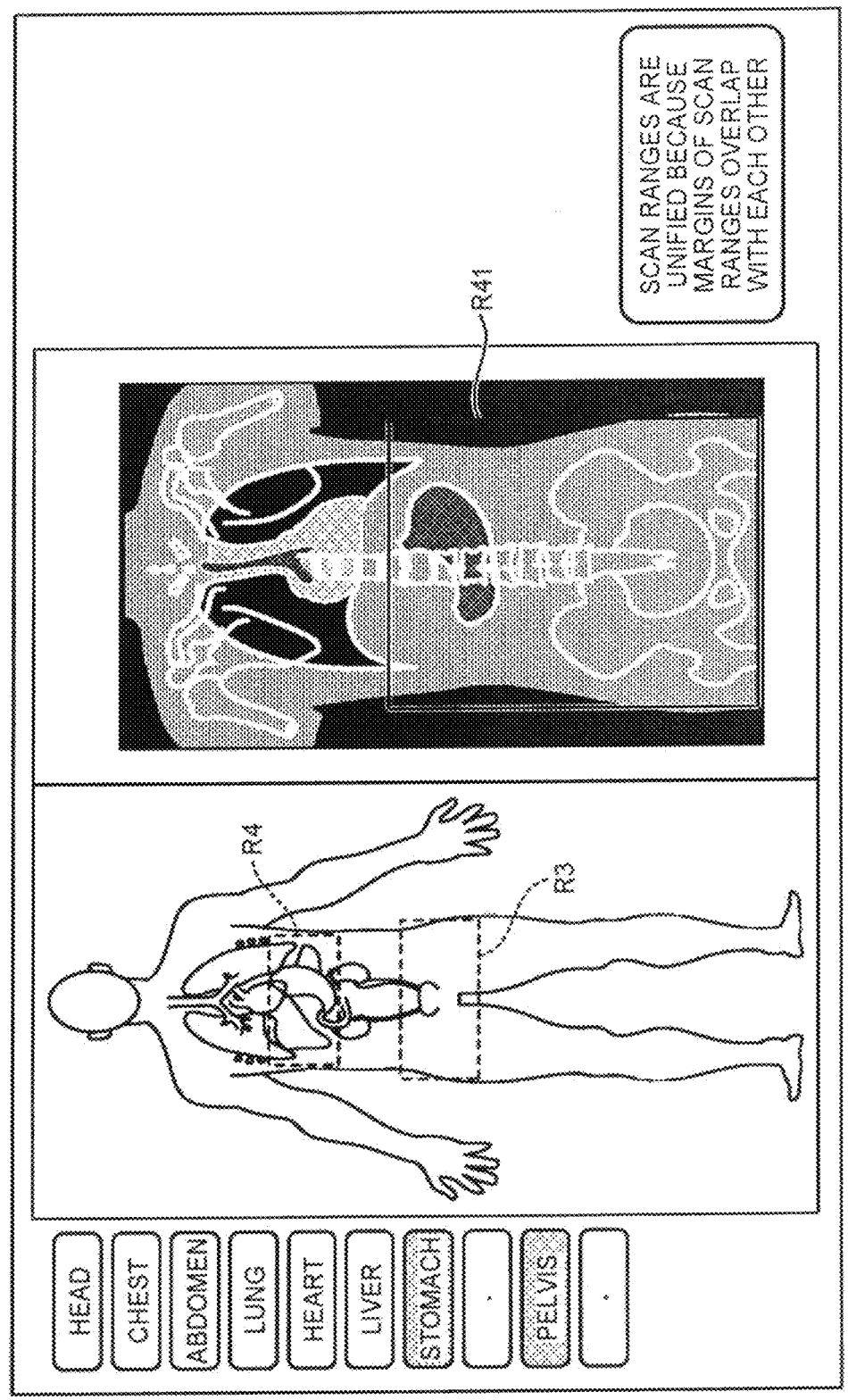
FIG. 9B is a diagram for explaining one example of scan range unification according to the present embodiment.

FIG. 9B is a diagram for explaining one example of scan range unification according to the present embodiment. For example, as shown in FIG. 9B, when a "stomach" and a "pelvis" are specified as scan subject parts, the scan position/range-changing processing unit 124 converts coordinate data of a scan range R4 corresponding to a "stomach" on a virtual patient image into coordinate data of a scan range in image data. Furthermore, the scan position/range-changing processing unit 124 convers coordinate data of a scan range R3 corresponding to a "pelvis" on the virtual patient image into coordinate data of a scan range in the image data.

Subsequently, similarly to the processing described above, the scan position/range-changing processing unit 124 determines whether X-ray irradiation regions overlap with each other when the scan range corresponding to a "stomach" and the scan range corresponding to a "pelvis" are scanned. When determining that the X-ray irradiation regions to scan the respective scan ranges overlap with each other including margins, the scan position/range-changing processing unit 124 sets a range R41 that is obtained by unifying the respective scan ranges as a scan range for main scanning as shown in FIG. 9B. As described, the margins are regions in which X-rays are irradiated, and the subject is exposed to radiation. Therefore, if exposed similarly to the scan range, by controlling to collect image data of that portion also, it is controlled to be able to acquire more image data with the same amount of radiation exposure.

When the scan range R41 is set by the scan position/range-changing processing unit 124, the host controller 110 controls to display, on the display device 116, a result of scan range setting as "SCAN RANGES ARE UNIFIED BECAUSE MARGINS OF SCAN RANGES OVERLAP WITH EACH OTHER" as shown in FIG. 9B, together with a reason for the setting.

As described above, when more than one scan subject part is specified, the X-ray computed-tomography apparatus according to the present embodiment divides or unifies scan ranges to scan respective subject parts based on X-ray irradiation regions. As for division and unification of scan regions, although a case of scan ranges to scan subject parts that are at different positions in a subject has been explained, embodiments are not limited thereto, and division may be done chronologically for subject parts at the same position in a subject.

For example, when scanning is performed using a contrast agent, the host controller 110 can determine whether to divide also according to timing over a course of injecting the contrast agent. As one example, the host controller 110 controls to perform scanning dividing into a point of time soon after injection of the contrast agent is started, and a point of time when time has passed from the start of injection of the contrast agent.

Next, one embodiment applying a technique of the present application in which characteristic points in a virtual patient image and characteristic points in image data are checked against each other is explained. In X-ray computed-tomography apparatuses, as a technique of determining scan start timing according to the density of contrast agent when contrast scanning is performed, a technique in which preliminary scanning (also called Real Prep, Prepscan, and Sure Start) is performed prior to scanning to acquire images for diagnosis, and start timing of main scanning is controlled based on a time-varying curve of CT values that are measured by this preliminary scanning has been known.

For example, in the above technique, first, image data is acquired with small dose, and a region of interest (ROI) to observe variation of CT values with time is set for the acquired image data. When the CT value in the ROI exceeds a threshold, main scanning is started. In this example, the ROI is set to a blood vessel at an upstream position of a scan subject part, and there is a case in which it is difficult to set an ROI at an accurate position. By applying the technique of the present application, it becomes possible to set an ROI to an accurate position easily.

Specifically, the scan position/range-changing processing unit 124 changes a region of interest to detect a flowing state of a contrast agent predetermined for a virtual subject into a region of interest on a positioning image based on a result of checking by the position-check processing unit 123. The host controller 110 detects the density of the contrast agent in a region corresponding to the region of interest on the positioning image in image data that is acquired by preliminary scanning to determine start timing for main scanning using a contrast agent, and controls to start main scanning when the detected density of the contrast agent exceed a predetermined threshold.

Figure 10:
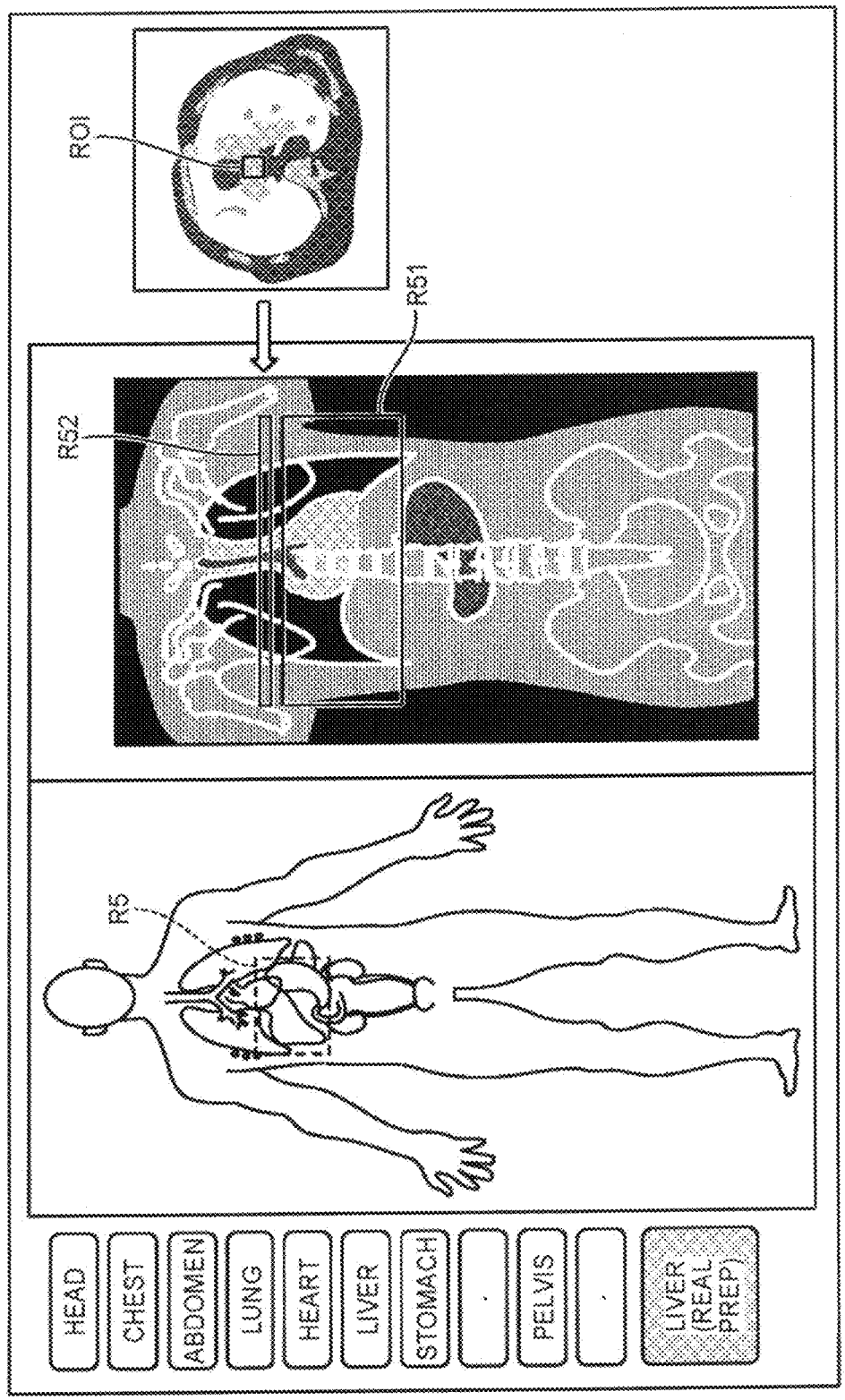
FIG. 10 is a diagram for explaining one example of contrast scanning according to the present embodiment.

FIG. 10 is a diagram for explaining one example of contrast scanning according to the present embodiment. FIG. 10 indicates a case of scanning "liver" with "Real Prep". For example, as shown in FIG. 10, when a button of "liver" with "Real Prep" is pressed, the host controller 110 outputs data of a range R5 corresponding to the button "liver" with "Real Prep" to the scan position/range-changing processing unit 124. When specification is made for a part with "Real Prep", the host controller 110 also outputs ROI data set for each part in advance to the scan position/range-changing processing unit 124.

The ROI data described above is ROI data that is set for an ROI set on a virtual patient image by an experienced technician or doctor. That is, an experience technician or doctor sets an optimal ROI for each part in advance at the time of performing "Real Prep", to be stored in the storage device 112. The host controller 110 reads coordinate data of the ROI corresponding to the specified part "liver" from the storage device 112, and outputs to the scan position/range-changing processing unit 124 together with the coordinate data of the range R5 corresponding to "liver". The scan position/range-changing processing unit 124 changes the coordinate data accepted from the host controller 110 using the coordinate transformation matrix into coordinate data in the positioning image, and sets a scan range R51 corresponding to "liver" and a scan range R52 including the ROI as shown in FIG. 10.

As described, by changing coordinate data of a virtual patient image into coordinate data in image data of the subject using the coordinate transformation matrix acquired for each subject, an accurate position of ROI that has been set on a virtual patient image by an experience technician or doctor is reflected accurately on respective image data of a subject, and thereby enabling to make accurate setting of ROI easily. When an ROI is set by the scan position/range-changing processing unit 124, for example, the host controller 110 controls the display device 116 to display the set ROI on an axial plane as shown in FIG. 10, and makes an operator determine whether there is no problem in the ROI setting. When determining that there is no problem in the ROI setting, the operator inputs an instruction to perform "Real Prep" through the input device 115. Thus, contrast scanning of a "liver" is performed by "Real Prep".

As described above, in the technique of the present application, by checking anatomical characteristic points in a virtual patient image and characteristic points in image data of a subject against each other, and by matching characteristic points that are supposed to correspond with each other, a coordinate transformation matrix is acquired. In the technique of the present application, the accuracy of matching for characteristic points is important. Therefore, to improve the accuracy of matching, the following processing can also be performed.

Specifically, the host controller 110 performs correction processing for checking data relating to characteristic points based on a structure inside the subject and data relating to anatomical characteristic points corresponding to a virtual subject, on image data of a subject acquired by positioning scanning or projection data that is used to reconstruct image data. For example, the host controller 110 performs noise reduction processing or metal artifact removal processing on image data collected from a subject or projection data to improve the image quality of image data used for matching, thereby improving the accuracy of matching. As one example, the host controller 110 controls the volume-reconstruction processing unit 118 to perform successive approximation reconstruction to reduce noises.

Moreover, as another method of improving the accuracy, the volume-reconstruction processing unit 118 reconstructs image data based on projection data that is acquired successively by positioning scanning during the positioning scanning. The host controller 110 detects start of scanning of a predetermined part based on image data that is acquired during the positioning scanning, and controls the high-voltage generating device 109 to modulate a tube current value during the positioning scanning based on a result of detection. That is, the volume-reconstruction processing unit 118 reconstructs image data in real time during the positioning scanning. The anatomical-landmark detecting unit 122 sequentially detects a part included in the image data reconstructed in real time. The host controller 110 changes to a scan condition optimal to each part detected by the anatomical-landmark detecting unit 122. Thus, high quality image data can be acquired for each part to perform matching.

As one example, the host controller 110 sets the tube current value to "10 mA" when a "lung" is scanned, and modulates the tube current value to "20 mA" when detecting a "liver". That is, if a "liver" is scanned under the same condition as a "lung" having air inside, noises increase and the image quality sufficiently high cannot be obtained. Therefore, when a "liver" is detected during scanning of a "lung", the scan condition is changed upon detection. At this point, if the tube current value is modulated after a part of a "liver" is detected, it can be too late. Therefore, the host controller 110 starts modulating the tube current value, for example, when a scan position passes a position in the middle of a "heart". This enables to acquire a sufficient tube current value by the time of scanning a "liver". As described, when processing in real time, the host controller makes projections about parts.

Furthermore, the scan condition that is changed in real time is not only the tube current value, and the how-tie filter and a collimator can be controlled also. Specifically, the host controller 110 detects start of scanning of a predetermined part based on image data that is acquired during positioning scanning, and arranges a bow-tie filter corresponding to the predetermined part on an irradiation line of an X-ray irradiated from the X-ray tube, based on a result of the detection.

As described above, by detecting a part in real time, and by changing various scan conditions for each part, higher quality image data can be collected to perform matching. In the above example, a case in which detection of a part in real time is performed by ALD has been explained. However, embodiments are not limited thereto, and other arbitrary methods can be applied. As one example, a part can be detected by comparing a sinogram in a virtual patient image and a sinogram in three-dimensional data collected from a subject.

For example, because a sinogram of a "lung" and a sinogram of a "liver" significantly differ from each other, a "liver" can be detected based on the difference. Alternatively, to make a projection, a "liver" can be detected based on a difference between a sinogram of a "lung" and a sinogram of a "heart". Moreover, detection of parts may be performed by comparing with a learning image in which a large number of sinograms are learned. That is, sinograms indicating respective parts are learned by using projection images that are actually collected, and the learned sinograms and a sinogram of a subject may be compared. As described above, by detecting a part using sinograms, processing can be done with increased speed compared to a case applying ALD.

Figure 11:
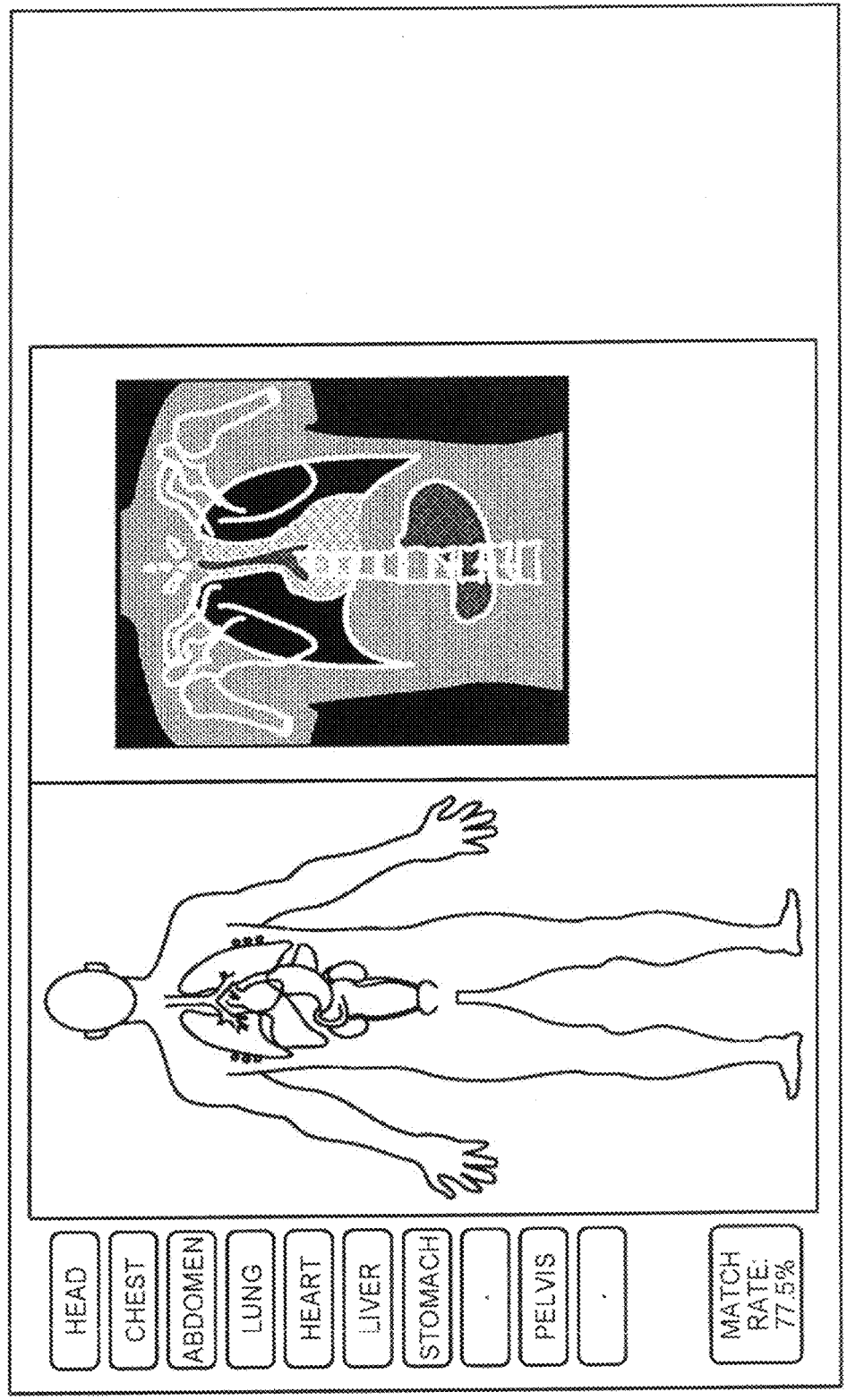
FIG. 11 shows a display example of a matching result according to the present embodiment.
Figure 13:
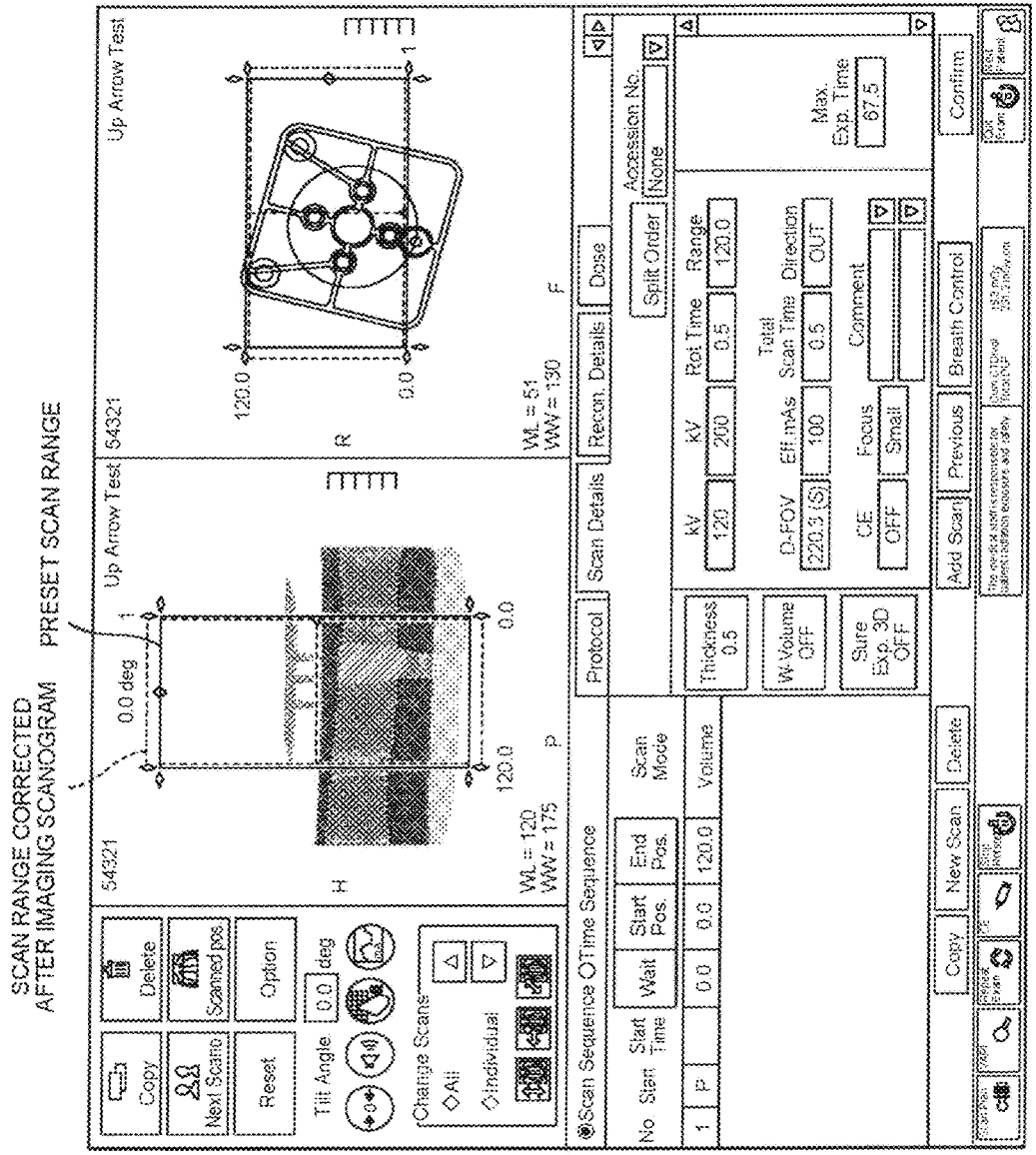
FIG. 13 shows an example of a conventional protocol preset screen.

Furthermore, a result of matching described above can be displayed on the display device 116. FIG. 11 shows a display example of a matching result according to the present embodiment. For example, the host controller 110 displays "match rate: 77.5%" as a matching result of characteristic points in a virtual patient image and characteristic points in image data as shown in FIG. 11. The match rate indicates to what extent the characteristic points that correspond with anatomical characteristic points included at a scan position or in a scan range specified on a virtual patient image are found in image data.

As one example, the match rate indicates how many characteristic points are matched among anatomical characteristic points included at a scan position or in a scan range specified on a virtual patient image. Alternatively, the match rate indicates an average of accuracy of respective matched characteristic points. This enables an observer to recognize how accurately the setting of the scan range has been performed at main scanning. For example, when the match rate is low, an operator can perform processing to improve the matching accuracy described above by operating the input device 115.

In the embodiment described above, a case in which positioning scanning is performed, and matching of anatomical characteristic points in a virtual patient image and anatomical characteristic points in a positioning image is performed has been explained. However, embodiments are not limited thereto, and for example, it may take a case in which positioning scanning is not performed. In such a case, for example, the anatomical-landmark detecting unit 122 detects, during main scanning, a part included in image data by performing ALD on image data that is collected by the main scanning.

Subsequently, the position-check processing unit 123 checks correspondence between the virtual patient image and the image data in which a part is detected, and calculates a coordinate transformation matrix. When detecting, in the image data collected by the main scanning, a part corresponding to a part specified on the virtual patient image, the scan position/range-changing processing unit 124 outputs a signal to stop the main scanning to the host controller 110. Upon receiving the signal, the host controller 110 controls to stop the main scanning. Thus, main scanning of a desirable part can be automatically stopped. A position of a projector may be set in a virtual patient image, and may be used as a start of main scanning.

As for an imaging-condition-setting support apparatus, it is configured with the storage device 112, the input device 115, the display device 116, the scan-plan expert system 120, the virtual-patient-image data storage unit 121, the anatomical-landmark detecting unit 122, the position-check processing unit 123, and the scan position/range-changing processing unit 124.

Figure 14:
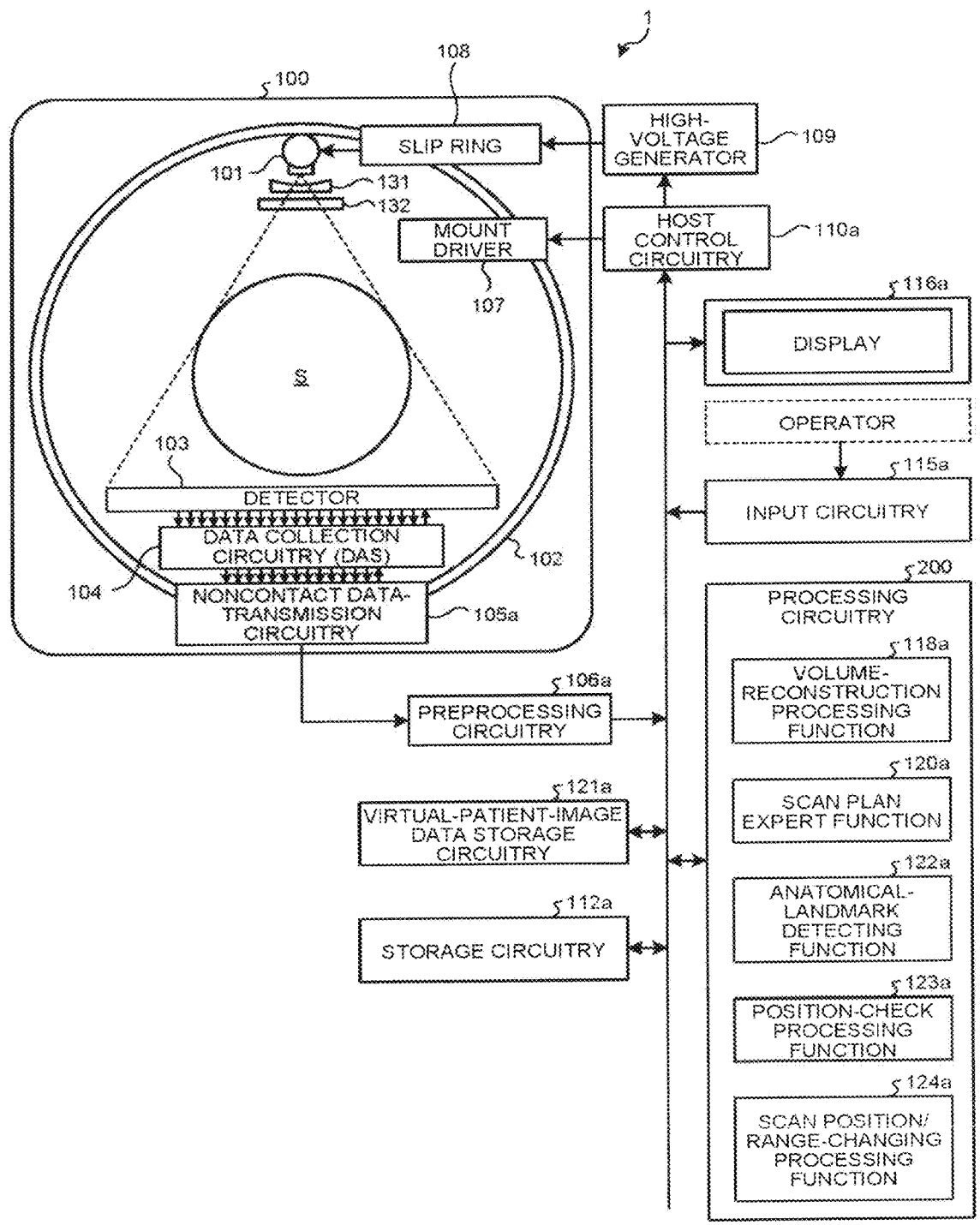
FIG. 14 is a diagram that illustrates an example of the configuration of an X-ray computer tomographic apparatus according to another embodiment

Here, another embodiment of the X-ray computer tomographic apparatus described above will be described with reference to FIG. 14. FIG. 14 is a diagram that illustrates an example of the configuration of an X-ray computer tomographic apparatus 1 according to another embodiment. In another embodiment, the points different from the above embodiments are mainly explained, and as for functions similar to the components explained in the above embodiment, the same reference numerals are given thereto, and explanation thereof is omitted. As illustrated in FIG. 14, the X-ray computer tomographic apparatus 1 according to the other embodiment includes a gantry 100, preprocessing circuitry 106a, a high voltage generator 109, host control circuitry 110a, storage circuitry 112a, virtual patient image data storage circuitry 121a, a display 116a, input circuitry 115a and processing circuitry 200. As illustrated in FIG. 14, each circuitry is connected in each other and to transmit and receive various signals to each other. The preprocessing circuitry 106a corresponds to preprocessing device 106 illustrated in FIG. 1. The host control circuitry 110a corresponds to the host controller 110 illustrated in FIG. 1. The storage circuitry 112a corresponds to the storage device 112 illustrated in FIG. 1. The virtual patient image data storage circuitry 121a corresponds to the virtual patient image data storage unit 121 illustrated in FIG. 1. The display 116a corresponds to the display device 116 illustrated in FIG. 1. The input circuitry 115a corresponds to the input device 115 illustrated in FIG. 1.

The gantry 100 includes an X-ray tube 101, a rotational frame 102, an X-ray detector 103, data collection circuitry 104, noncontact data transmission circuitry 105a, a mount driver 107, a slip ring 108, a bow tie filter 131, and a collimator 132. In the embodiment in FIG. 14, the respective processing functions performed by the noncontact data transmission device 105, the pre-processing device 106, the host controller 110, the volume reconstruction processing unit 118, the scan plan expert system 120, the anatomical landmark detecting unit 122, the position check processing unit 123, and the scan position/range changing processing unit 124 illustrated in FIG. 1 are stored in a storage circuitry 112a or a storage circuitry not illustrated, in the form of a computer-executable program. The noncontact data transmission circuitry 105a corresponds to the noncontact data transmission device 105 illustrated in FIG. 1.

Each of the data collection circuitry 104, the noncontact data transmission circuitry 105a, the preprocessing circuitry 106a, the host control circuitry 110a and the processing circuitry 200 is a processor that loads programs from the storage circuitry 112a or a storage circuitry not illustrated in FIG. 14, and executes the programs so as to implement the respective functions corresponding to the programs. In other words, each circuitry that has loaded the programs has the functions corresponding to the programs loaded. The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions.

The storage circuitry 112a, for example, stores therein computer programs corresponding to a volume reconstruction processing function 118a, a scan plan expert function 120a, an anatomical landmark detecting function 122a, a position check processing function 123a, and a scan position/range changing processing function 124a. The processing circuitry 200 reads the program corresponding to the volume reconstruction processing function 118a from the storage circuitry 112a and executes the program, thereby performing processing similar to the volume reconstruction processing unit 118a. The processing circuitry 200 reads the program corresponding to the scan plan expert function 120a from the storage circuitry 112a and executes the program, thereby performing processing similar to the scan plan expert system 120. The processing circuitry 200 reads the program corresponding to the anatomical landmark detecting function 122a from the storage circuitry 112a and executes the program, thereby performing processing similar to the anatomical landmark detecting unit 122. The processing circuitry 200 reads the program corresponding to the position check processing function 123a from the storage circuitry 112a and executes the program, thereby performing processing similar to the position check processing unit 123. The processing circuitry 200 reads the program corresponding to the scan position/range changing processing function 124a from the storage circuitry 112a and executes the program, thereby performing processing similar to the scan position/range changing processing unit 124.

The storage circuitry 112a, for example, stores therein computer programs corresponding to a host control function to control the entire apparatus. The host control circuitry 110a reads the program corresponding to the host control function from the storage circuitry 112a and executes the program, thereby performing processing similar to the host controller 110. The storage circuitry 112a or the storage circuitry non-illustrated, for example, stores therein computer programs corresponding to a data collection function, a noncontact data transmission function and a preprocessing function. The data collection circuitry 104, the noncontact data transmission circuitry 105a and the preprocessing circuitry 106a read the programs corresponding to the data collection function, the noncontact data transmission function and the preprocessing function from the storage circuitry 112a or the storage circuitry non-illustrated, and execute the program, thereby performing processing similar to The data collection circuit 104, the noncontact data transmission device 105 and the preprocessing device 106.

The example illustrated in FIG. 14 describes a case of implementing the volume reconstruction processing function 118a, the scan plan expert function 120a, the anatomical landmark detecting function 122a, the position check processing function 123a, and the scan position/range changing processing function 124a by causing one processing circuitry 200 to execute the respective programs. However, embodiments are not so limited, and for example, a plurality of processing circuits may implement the volume reconstruction processing function 118a, the scan plan expert function 120a, the anatomical landmark detecting function 122a, the position check processing function 123a, and the scan position/range changing processing function 124a. For example, one or more functions among the volume reconstruction processing function 118a, the scan plan expert function 120a, the anatomical landmark detecting function 122a, the position check processing function 123a, and the scan position/range changing processing function 124a may be separately implemented in exclusive, independent program execution circuits.

Some of the circuitry illustrated in FIG. 14 may be implemented as one processing circuit. For example, one program execution circuit may implement the host control function implemented by the host control circuitry 110a and the volume reconstruction processing function 118a, the scan plan expert function 120a, the anatomical landmark detecting function 122a, the position check processing function 123a, and the scan position/range changing processing function 124a implemented by the processing circuitry 200.

The input circuitry 115a is implemented by a trackball, a switch button, a mouse, a keyboard, or the like for performing the setting of a scan position and a scan range or the like. The input circuitry 115a is connected to the host control circuitry 110a, converts input operation received from an operator into an electric signal, and outputs the electric signal to the host control circuitry 110a or the processing circuitry 200.

Figure 15:
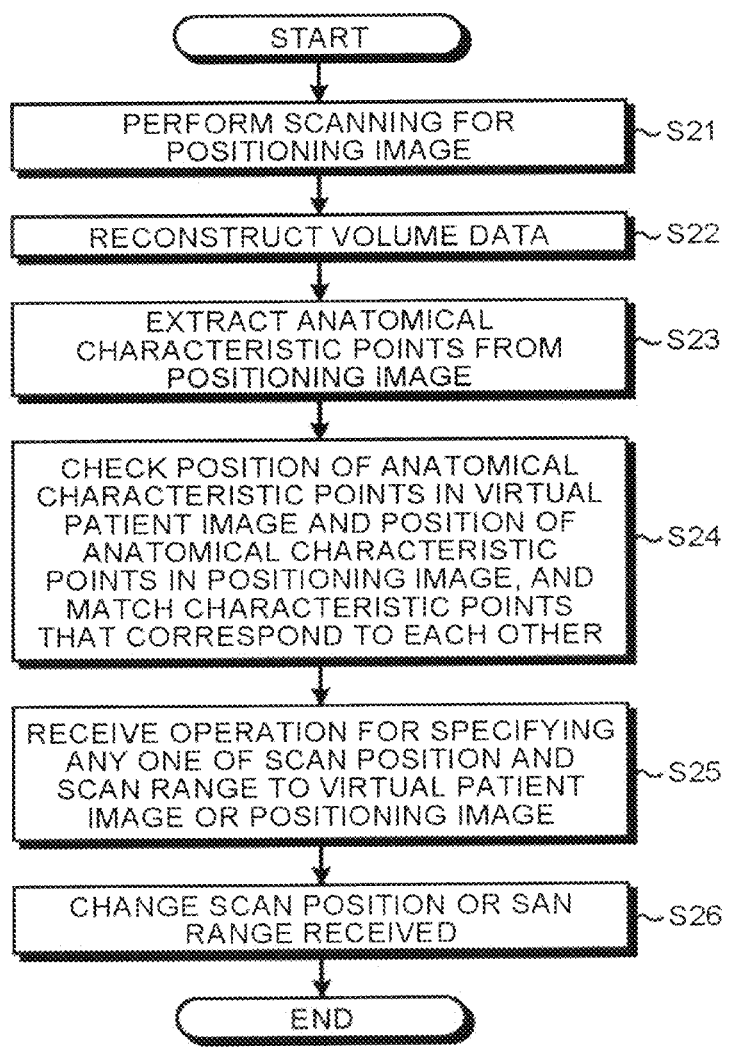
FIG. 15 is a flowchart illustrating a procedure of processing performed by the X-ray computer tomographic apparatus in the present embodiment

The following describes a processing procedure in the present embodiment with reference to FIG. 15. FIG. 15 is a flowchart illustrating a procedure of processing performed by the X-ray computer tomographic apparatus in the present embodiment. In FIG. 15, a case in which operation for specifying any one of scan position and scan range to the virtual patient image or the positioning image is received after positioning scanning is illustrated. However, embodiments are not limited thereto, and for example, it may take a case in which positioning scanning is performed after receiving of the operation.

Step S21 in FIG. 15 is a step implemented by causing the host control circuitry 110a to read the program corresponding to the host control function from the storage circuitry 112a and to execute the program. At Step S21, the host control circuitry 110a controls the mount driver 107, the high-voltage generator 109, and the like, thereby performing position scanning. Step S22 in FIG. 15 is a step implemented by causing the processing circuitry 200 to read the program corresponding to the volume reconstruction processing function 118a from the storage circuitry 112a and to execute the program. At Step S22, the processing circuitry 200 reconstructs volume data from the projection data stored in the storage circuitry 112a.

Step S23 in FIG. 15 is a step implemented by causing the processing circuitry 200 to read the program corresponding to the anatomical landmark detecting function 122a from the storage circuitry 112a and to execute the program. At step S23, the processing circuitry 200 executes anatomical characteristic points from the positioning image based on structural characteristics and the like by image processing such as pattern recognition. Step S24 in FIG. 15 is a step implemented by causing the processing circuitry 200 to read the program corresponding to the position check processing function 123a from the storage circuitry 112a and to execute the program. At Step S24, the processing circuitry 200 checks position of anatomical characteristic points in virtual patient image and position of anatomical characteristic points in positioning image, and match characteristic points that correspond to each other.

Step S25 in FIG. 15 are steps implemented by causing the input circuitry 115a. At Steps S25, the input circuitry 115a receives an operation for specifying any one of scan position and scan range to virtual patient image or positioning image.

Step S26 in FIG. 15 are steps implemented by causing the processing circuitry 200 to read the program corresponding to the scan position/range changing processing function 124a from the storage circuitry 112a and to execute the program. At step S26, the processing circuitry 200 changes scan position or scan range received from the input circuitry 115a based on a result of checking position of anatomical characteristic points. For example, the processing circuitry 200 changes a scan position or a scan range specified on the virtual patient image into a scan position or a scan range on the positioning image. The processing circuitry 200 also changes a scan position or a scan range specified on the positioning image into a scan position or a scan range on the virtual patient image. The above-described processing circuitry 200 is an example of a processing circuitry in the claims.

As explained above, according to the embodiment, the accuracy of preset of an imaging position and the like can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed-tomography apparatus comprising:
an X-ray tube;
a high-voltage generator configured to generate a tube voltage to be applied to the X-ray tube;
an X-ray detector configured to detect an X-ray that is irradiated from the X-ray tube, and that has passed through a subject;
a rotation frame configured to support the X-ray tube in a rotatable manner around the subject; and
processing circuitry configured to
control the high-voltage generator and the rotation frame to perform positioning scanning and main scanning on the subject,
reconstruct image data based on projection data that is generated by an output of the X-ray detector,
select a virtual subject and specify any one of a scan position and a scan range to the virtual subject for the main scanning, before any acquisition of the image data, and
identify a characteristic point based on a structure inside the subject from the image data, and change any one of the scan position and the scan range specified to any one of a scan position and a scan range for the main scanning, based on a result of checking data relating to the identified characteristic point and data relating to a corresponding anatomical characteristic point in the virtual subject against each other.

2. The X-ray computed-tomography apparatus according to claim 1, wherein
the processing circuitry is further configured to perform, on any one of image data of the subject that is acquired by the positioning scanning and projection data that is used to reconstruct the image data, correction processing for checking data relating to a characteristic point based on a structure inside the subject and data relating to a corresponding anatomical characteristic point in a virtual subject against each other.

3. The X-ray computed-tomography apparatus according to claim 1, wherein
the processing circuitry is configured to
reconstruct, during the positioning imaging, image data based on projection data that is successively acquired in the positioning scanning, and
detect a start of scanning of a predetermined part based on image data that is acquired during the positioning scanning, and control the high-voltage generator to modulate a tube voltage value during the positioning scanning, based on a result of the detection.

4. The X-ray computed-tomography apparatus according to claim 1, wherein
the processing circuitry is configured to
reconstruct, during the positioning imaging, image data based on projection data that is successively acquired in the positioning scanning, and
detect a start of scanning of a predetermined part based on image data that is acquired during the positioning scanning, and arrange a bow-tie filter corresponding to the predetermined part on an irradiation line of an X-ray that is irradiated from the X-ray tube device based on a result of the detection.

5. X-ray computed-tomography apparatus according to claim wherein
the processing circuitry is configured to perform specification by an operator specifying any one of a scan position and a scan range on any one of a virtual patient image and an actual image of the subject by using an input circuitry.

6. The X-ray computed-tomography apparatus according to claim 1, wherein
the processing circuitry is configured to perform specification by acquiring data relating to a scan subject part based on request data from an examination-request data system, and by specifying any one of a scan position and a scan range that corresponds to the scan subject part.

7. The X-ray computed-tomography apparatus according to claim 1, wherein
the processing circuitry is configured to control to perform main scanning on the subject according to any one of the scan position and the scan range that has been changed set.

8. The X-ray computed-tomography apparatus according to claim 1, wherein
the processing circuitry is configured to
specify any one of a reconstruction position and a reconstruction range on a virtual patient image,
change any one of the reconstruction position and the reconstruction range that is specified on the virtual patient image based on a result of the checking, and
reconstruct image data of any one of the reconstruction position and the reconstruction range changed.

9. The X-ray computed-tomography apparatus according to claim 1, wherein
the processing circuitry is configured to acquire a coordinate transformation matrix that minimizes a positional gap between a plurality of anatomical characteristic points that are expressed on a coordinate system of a virtual patient image and a plurality of characteristic points that are expressed on a coordinate system of a positioning image, and change any one of a scan position and a scan range that is specified on the virtual patient image into any one of a scan position and a scan range that is expressed on a coordinate system of the positioning image by the coordinate transformation matrix.

10. The X-ray computed-tomography apparatus according to claim 1, wherein
a mark that indicates any one of the scan position and the scan range changed set is displayed on a positioning image in an overlapped manner.

11. The X-ray computed-tomography apparatus according to claim 1, further comprising:
storage circuitry configured to store data of a plurality of virtual patient images; and
a display is configured to display one piece of a virtual patient image selected based on subject data of the subject and read from the storage circuitry.

12. The X-ray computed-tomography apparatus according to claim 1, wherein
the processing circuitry is configured to adjust any one of the scan position and the scan range based on at least one of a scan condition that is set per facility and a scan time that is set per subject.

13. The X-ray computed-tomography apparatus according to claim 1, wherein
the processing circuitry is configured to divide or unify a scan range, when a plurality of scan subject parts are included at main scanning on the subject, based on positional relation of X-ray irradiation regions to scan the respective scan subject parts.

14. The X-ray computed-tomography apparatus according to claim 13, wherein
the processing circuitry is configured to divide a scan range, when X-ray irradiation regions to scan the respective scan subject parts are distant from each other, so that the respective scan subject parts are scanned independently, and unify scan ranges, when X-ray irradiation regions to scan the respective scan subject parts overlap with each other, so that the respective scan subject parts are scanned collectively.

15. The X-ray computed-tomography apparatus according to claim 1, wherein
the processing circuitry is configured to divide a scan time for the main scanning based on a density of contrast agent at a scan subject part.

16. The X-ray computed-tomography apparatus according to claim 1, further comprising
the processing circuitry is further configured to calculate a match rate when data relating to characteristic points based on a structure inside the subject and data relating to corresponding anatomical characteristic points in a virtual subject are checked against each other, and cause a display to display the calculated match rate.

17. The X-ray computed-tomography apparatus according to claim 1, wherein
the processing circuitry is configured to
change a region of interest to detect an injected state of a contrast agent set in advance for the virtual subject into a region of interest on a positioning image based on a result of the checking, and
detect, in image data that is acquired in preliminary scanning to determine start timing of main scanning using a contrast agent, a density of the contrast agent in a region corresponding to the region of interest on the positioning image, and control to start the main scanning when the detected density of the contrast agent exceeds a threshold.

18. An imaging-condition-setting support apparatus, comprising:
processing circuitry is configured to
select a virtual subject and specify any one of a scan position and a scan range to the virtual subject for main scanning of a subject, before any acquisition of image data; and
identify characteristic points based on a structure inside the subject from image data reconstructed based on projection data that is generated from output of an X-ray detector, and change any one of the scan position and the scan range specified to any one of a scan position and a scan range for the main scanning, based on a result of checking data relating to the identified characteristic points and data relating to corresponding anatomical characteristic points in the virtual subject against each other.

* * * * *